(12) United States Patent
Edge et al.

(10) Patent No.: US 8,921,642 B2
(45) Date of Patent: Dec. 30, 2014

(54) CONDITIONAL-STOP DIMERIZABLE CASPASE TRANSGENIC ANIMALS

(75) Inventors: Albert Edge, Brookline, MA (US); Masato Fujioka, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 754 days.

(21) Appl. No.: 12/352,515

(22) Filed: Jan. 12, 2009

(65) Prior Publication Data
US 2009/0193533 A1  Jul. 30, 2009

Related U.S. Application Data

(60) Provisional application No. 61/020,666, filed on Jan. 11, 2008.

(51) Int. Cl.
| | | |
|---|---|---|
| *A01K 67/033* | (2006.01) | |
| *C12N 15/00* | (2006.01) | |
| *C12N 5/00* | (2006.01) | |
| *C12N 5/073* | (2010.01) | |
| *A01K 67/027* | (2006.01) | |
| *C12N 15/85* | (2006.01) | |
| *C12N 9/64* | (2006.01) | |
| *C12N 9/90* | (2006.01) | |

(52) U.S. Cl.
CPC ....... *C12N 15/8509* (2013.01); *A01K 2217/206* (2013.01); *A01K 2267/0362* (2013.01); *A01K 67/0275* (2013.01); *C12N 2840/002* (2013.01); *A01K 2217/15* (2013.01); *C07K 2319/70* (2013.01); *A01K 2217/30* (2013.01); *A01K 2217/203* (2013.01); *C12N 2800/30* (2013.01); *A01K 2227/105* (2013.01); *A01K 2267/03* (2013.01); *C12N 9/6475* (2013.01); *A01K 2217/072* (2013.01); *C12N 9/90* (2013.01)
USPC .................. 800/18; 800/13; 800/21; 800/22; 800/25; 435/325

(58) Field of Classification Search
USPC ..................... 800/18, 13, 21, 22, 25; 435/325
See application file for complete search history.

(56) References Cited

U.S. PATENT DOCUMENTS

| | | | |
|---|---|---|---|
| 4,894,366 A | 1/1990 | Okuhara et al. | |
| 5,091,389 A | 2/1992 | Ondeyka et al. | |
| 5,093,338 A | 3/1992 | Byrne et al. | |
| 5,109,112 A | 4/1992 | Siekierka et al. | |
| 5,116,756 A | 5/1992 | Dumont et al. | |
| 5,140,018 A | 8/1992 | Klein et al. | |
| 5,147,877 A | 9/1992 | Goulet | |
| 5,198,421 A | 3/1993 | Chen et al. | |
| 5,200,411 A | 4/1993 | Edmunds et al. | |
| 5,208,241 A | 5/1993 | Ok et al. | |
| 5,210,030 A | 5/1993 | Petuch et al. | |
| 5,221,625 A | 6/1993 | Chen et al. | |
| 5,225,403 A | 7/1993 | Treiber et al. | |
| 5,247,076 A | 9/1993 | Goulet et al. | |
| 5,252,732 A | 10/1993 | Sinclair et al. | |
| 5,258,389 A | 11/1993 | Goulet et al. | |
| 5,310,901 A | 5/1994 | Parsons et al. | |
| 5,310,903 A | 5/1994 | Goulet et al. | |
| 5,318,895 A | 6/1994 | Kahn et al. | |
| 5,324,644 A | 6/1994 | Ruby et al. | |
| 5,362,718 A | 11/1994 | Skotnicki et al. | |
| 5,362,735 A | 11/1994 | Luengo | |
| 5,457,182 A | 10/1995 | Wiederrecht et al. | |
| 5,457,194 A | 10/1995 | Luly et al. | |
| 5,484,799 A | 1/1996 | Hochlowski et al. | |
| 5,516,781 A | 5/1996 | Morris et al. | |
| 5,527,907 A | 6/1996 | Or et al. | |
| 5,534,632 A | 7/1996 | Or et al. | |
| 5,541,189 A | 7/1996 | Luly et al. | |
| 5,541,193 A | 7/1996 | Kawai et al. | |
| 5,561,137 A | 10/1996 | Or et al. | |
| 5,561,228 A | 10/1996 | Or et al. | |
| 5,563,172 A | 10/1996 | Wagner et al. | |
| 5,583,139 A | 12/1996 | Or et al. | |
| 5,597,715 A | 1/1997 | Ford | |
| 5,604,234 A | 2/1997 | Or et al. | |
| 5,665,772 A | 9/1997 | Cottens et al. | |
| 6,384,046 B1 | 5/2002 | Schuler et al. | |
| 6,689,937 B2 * | 2/2004 | Hui et al. ............................ 800/3 |
| 2002/0170076 A1 | 11/2002 | Dymecki | |
| 2005/0272132 A1 | 12/2005 | Gregory et al. | |
| 2006/0078980 A1 | 4/2006 | Gregory et al. | |
| 2006/0194829 A1 | 8/2006 | Clackson et al. | |

FOREIGN PATENT DOCUMENTS

| | | |
|---|---|---|
| EP | 551 182 | 7/1993 |
| EP | 568 310 | 11/1993 |
| EP | 691 130 | 1/1996 |
| WO | WO 92/05179 | 4/1992 |
| WO | WO 92/14737 | 9/1992 |
| WO | WO 93/04680 | 3/1993 |
| WO | WO 93/10122 | 5/1993 |
| WO | WO 93/11130 | 6/1993 |
| WO | WO 93/13663 | 7/1993 |
| WO | WO 93/18043 | 9/1993 |

(Continued)

OTHER PUBLICATIONS

Wencker et al., A mechanistic role for cardiac myocyte apoptosis in heart failure. J Clin Invest. May 15, 2003; 111(10): 1497-1504.*
Akimoto et al., Transgenic Mice Expressing Cre-Recombinase Specifically in M- or S-Cone Photoreceptors Investigative Ophthalmology and Visual Science. 2004;45:42-47.).*

(Continued)

*Primary Examiner* — Maria Leavitt
(74) *Attorney, Agent, or Firm* — Fish & Richardson P.C.

(57) ABSTRACT

Described are transgenic animals for conditional and inducible cell targeting, that express a dimerizable conditional-STOP caspase 3 transgene.

19 Claims, 16 Drawing Sheets

(56) References Cited

FOREIGN PATENT DOCUMENTS

| | | |
|---|---|---|
| WO | WO 93/25533 | 12/1993 |
| WO | WO 94/02136 | 2/1994 |
| WO | WO 94/02137 | 2/1994 |
| WO | WO 94/02485 | 2/1994 |
| WO | WO 94/04540 | 3/1994 |
| WO | WO 94/09010 | 4/1994 |
| WO | WO 94/10843 | 5/1994 |
| WO | WO 94/18207 | 8/1994 |
| WO | WO 94/21644 | 9/1994 |
| WO | WO 94/25022 | 11/1994 |
| WO | WO 95/04060 | 2/1995 |
| WO | WO 95/04738 | 2/1995 |
| WO | WO 95/07468 | 3/1995 |
| WO | WO 95/15328 | 6/1995 |
| WO | WO 95/16691 | 6/1995 |
| WO | WO 96/00282 | 1/1996 |
| WO | WO 96/03430 | 2/1996 |
| WO | WO 96/35423 | 11/1996 |
| WO | WO 96/41807 | 12/1996 |
| WO | WO 97/10502 | 3/1997 |
| WO | WO 03/064383 | 8/2003 |
| WO | WO 2004/026280 | 4/2004 |
| WO | WO 2004/078167 | 9/2004 |

OTHER PUBLICATIONS

Stricklett et al., Brief REVIEWThe Cre/loxP system and gene targeting in the kidney Am J Physiol Renal Physiol 276: F651-F657, 1999.*

Gossen et al., Studying Gene Function in Eukaryotes by Conditional Gene Inactivation Annual Review of Genetics vol. 36: 153-173 (Volume publication date Dec. 2002).*

Jonkers et al., "Conditional Mouse Models of Sporadic Cancer," *Nature Reviews/Cancer* 2:251-265, 2002.

Lasko et al, "Targeted Oncogene Activation by Site-Specific Recombination in Transgenic Mice," *Proc. Natl. Acad. Sci. U.S.A.* 89:6232-6236, 1992.

Ludwig et al., "Development of Mammary Adenocarcinomas by Tissue-Specific Knockout of Brca2 in Mice," *Oncogene* 20:3937-3948, 2001.

Sauer, "Inducible Gene Targeting in Mice using the Cre/Lox System," *Methods: A Companion to Methods in Enzymology* 14:381-392, 1998.

Ventura et al., "Cre-Lox-Regulated Conditional RNA Interference from Transgenes," *Proc. Natl. Acad. Sci. U.S.A.* 101(28):10380-10385, 2004.

"Inducible Mouse Models," Leiden University Medical Center (Jul. 2003).

Akagi et al., "Cre-mediated somatic site-specific recombination in mice," Nuc. Acids Res., 25(9):1766-1772 (1997).

Amara et al., "A versatile synthetic dimerizer for the regulation of protein-protein interactions," Proc. Natl. Acad. Sci. USA, 94:10618-10623 (1997).

Chow et al., "Inducible Cre recombinase activity in mouse cerebellar granule cell precursors and inner ear hair cells," Dev. Dyn., 235(11):2991-2998 (2006).

Clackson et al., "Redesigning an FKBP-ligand interface to generate chemical dimerizers with novel specificity," Proc. Natl. Acad. Sci. USA, 95:10437-10442 (1998).

Dymecki et al., "Using Flp-recombinase to characterize expansion of Wnt1-expressing neural progenitors in the mouse," Dev. Biol., 201(1):57-65 (1998).

Fellström et al., "Pathogenesis and treatment perspectives of chronic graft rejection (CVR)," Immunological Reviews, 134:83-98 (1993).

Fujitani et al., "Direct calculation of the binding free energies of FKBP ligands," J. Chem. Phys., 123(8):084108 (2005).

Gregory et al., "The use of new antiproliferative immunosuppressants is a novel and highly effective strategy for the prevention of vascular occulusive disease," J. Heart Lung Transpl., 11(11):197 (1992).

Hayashi et al., "Efficient recombination in diverse tissues by a tamoxifen-inducible form of Cre: a tool for temporally regulated gene activation/inactivation in the mouse," Dev. Biol., 244(2):305-318 (2002).

Hudak et al., "Design, Synthesis, and Biological Activity of Novel Polycyclic Aza-Amide FKBP12 Ligands," J. Med. Chem., 49(3):1202-1206 (2006).

Ikonen et al., "Sirolimus (rapamycin) halts and reverses progression of allograft vascular disease in non-human primates," Transplantation, 70(6):969-975 (2000).

Ivanova et al., "In vivo genetic ablation by Cre-mediated expression of diphtheria toxin fragment A," Genesis, 43:129-135 (2005).

Kahan, "The potential role of rapamycin in pediatric transplantation as observed from adult studies," Pediatr. Transplantation, 3:175-180 (1999).

Kang et al., "Caspase-8 serves both apoptotic and nonapoptotic roles," J. Immunol., 173(5):2976-2984,(2004).

Lasko et al., "Targeted oncogene activation by site-specific recombination in transgenic mice," Proc. Natl. Acad. Sci. USA, 89:6232-6236 (1992).

Lemberger et al., "Expression of Cre recombinase in dopaminoceptive neurons," BMC Neuroscience, 8:4 (2007).

Li et al., "Inner hair cell Cre-expressing transgenic mouse," Genesis, 39(3):173-177 (2004).

Lindeberg et al., "Transgenic expression of Cre recombinase from the tyrosine hydroxylase locus," Genesis, 40(2):67-73 (2004).

Ludwig et al. "FLP-mediated site-specific recombination in microinjected murine zygotes," Transgenic Res., 5(6):385-395 (1996).

Mallet et al., "Conditional cell ablation by tight control of caspase-3 dimerization in transgenic mice," Nat. Biotech., 20:1234-1239 (2002).

Matas et al., "Chronic rejection," J. Am. Soc. Nephrol., 4(1):S23-S29 (1994).

Meiser et al., "Effects of cyclosporin, FK506, and rapamycin on graft-vessel disease," The Lancet, 338:1297-1298 (1991).

Moeller et al., "An efficient system for tissue-specific overexpression of transgenes in podocytes in vivo," Am. J. Physiol. Renal. Physiol., 289(2):F481-F488 (2005).

Mollison et al., "Discovery of less nephrotoxic FK506 analogs and determining inamunophilin dependence of immunosuppressant nephrotoxicity with a novel single-dose rat cisplatin potentiation assay," J. Pharm. Exp. Ther., 283(3):1509-1519 (1997).

Morris et al., "Immunosuppressive effects of the morpholinoethyl ester of mycophenolic acid (RS-61443) in rat and nonhuman primate recipients of heart allografts," Transplant. Proc., 23(2):19-25 (1991).

Orban et al., "Tissue- and site-specific DNA recombination in transgenic mice," Proc. Natl. Acad. Sci. USA, 89(15):6861-6865 (1992).

Petros et al., "Conformation of two non-immunosuppressive FK506 analogs when bound to FKBP by isotope-filtered NMR," FEBS Lett., 308(3):309-314 (1992).

Pirvola et al., "FGFR1 is required for the development of the auditory sensory epithelium," Neuron, 35(4):671-680 (2002).

Pollack et al., "Regulation of gene expression with synthetic dimerizers," Methods Enzymol., 306:263-281 (1999).

Ray et al., "Development of a transgenic mouse model using rat insulin promoter to drive the expression of CRE recombinase in a tissue-specific manner," Int. J. Pancreatol., 25(3):157-163 (1999).

Rossant et al., ""Cre"-ating mouse mutants-a meeting review on conditional mouse genetics," Genes Dev., 13(2):142-145 (1999).

Sage et al., "Essential role of retinoblastoma protein in mammalian hair cell development and hearing," Proc. Nat. Acad. Sci. USA, 103(19):7345-7350 (2006).

Salmena et al., "Essential role for caspase 8 in T-cell homeostasis and T-cell-mediated immunity," Genes Dev., 17(7):883-895 (2003).

Sedrani et al., "Chemical modification of rapamycin: the discovery of SDZ RAD," Transplant. Proc., 30:2192-2194 (1998).

Somarelli et al., "Evolution of the 12 kDa FK506-binding protein gene," Biol. Cell, 99(6):311-321 (2007).

Spencer et al., "Controlling signal transduction with synthetic ligands," Science, 262:1019-10124 (1993).

(56) References Cited

OTHER PUBLICATIONS

Tian et al., "Creation of a transgenic mouse for hair-cell gene targeting by using a modified bacterial artificial chromosome containing Prestin," Dev. Dyn., 231(1):199-203 (2004).
Vooijs et al., "Flp-mediated tissue-specific inactivation of the retinoblastoma tumor suppressor gene in the mouse," Oncogene, 17(1):1-12 (1998).
Wang et al., "Targeted DNA recombination in vivo using an adenovirus carrying the cre recombinase gene," Proc. Natl. Acad. Sci. USA, 93:3932-3936 (1996).
Weiwad et al., "Comparative analysis of calcineurin inhibition by complexes of immunosuppressive drugs with human FK506 binding proteins," Biochemistry, 45(51):15776-15784 (2006).
Wilkinson et al., "Synthesis, molecular modeling and biological evaluation of aza-proline and aza-pipecolic derivatives as FICBP12 ligands and their in vivo neuroprotective effects," Bioorg. Med. Chem., 11:4815-4825 (2003).
Xiang et al., Essential role of POU-domain factor Brn-3c in auditory and vestibular hair cell development, Proc. Natl. Acad. Sci. USA, 94(17):9445-9450 (1997).
Xie et al., "Adenovirus-mediated tissue-targeted expression of a caspase-9-based artificial death switch for the treatment of prostate cancer," Cancer Res., 61(18):6795-6804 (2001).
Zecchini et al., "Notch signaling regulates the differentiation of post-mitotic intestinal epithelial cells," Genes Dev., 19(14):1686-1691 (2005).
Zhao et al., "FK506-binding protein ligands: structure-based design, synthesis, and neurotrophic/neuroprotective properties of substituted 5,5-dimethyl-2-(4-thiazolidine)carboxylates," J. Med. Chem. 49(14):4059-4071 (2006).
Zhao et al., "Modeling and synthesis of non-cyclic derivatives of GPI-1046 as potential FKBP ligands with neurotrophic properties," Bioorg. Med. Chem. Lett., 16(16):4385-4390 (2006).
ARIAD Pharmaceuticals, Inc., "ARGENT Regulated Homodimerization Kit," (2002).
Brockschniedier et al., "An improved mouse line for cre-induced cell ablation due to diphtheria toxin A, expressed from the Rosa26 locus," Genesis: The Journal of Genetics and Development, 44(7):322-327 (2006).
Chang et al., "Activation of Procaspases by FK506 Binding Protein-Mediated Oligomerization," Sci. STKE, 2003(167):11 (2003).
Extended European Search Report and Search Opinion issued in EP09700967 on Apr. 19, 2011.
International Preliminary Report on Patentability for International Application No. PCT/US09/30780, dated Jul. 13, 2010.
International Search Report for International Application No. PCT/US09/30780, dated Apr. 10, 2009.
Jaisser, Frederic, "Inducible Gene Expression and Gene Modification in Transgenic Mice," J. Am. Soc. Nephrol., 11:S95-S100 (2000).
Matsumura et al., "Lineage-specific cell disruption in living mice by Cre-mediated expression of diphtheria toxin A chain," Biochemical and Biophysical Research Communications, 321(2):275-279 (2004).
Pajvani et al., "Fat apoptosis through targeted activation of caspase 8: a new mouse model of inducible and reversible lipoatrophy," Nature Medicine, 11(7):797-803 (2005).
Rollins et al., "A ligand-reversible dimerization system for controlling protein-protein interactions," PNAS, 97:7096-7101 (2000).
Sato et al., Production of CETD transgenic mouse line allowing ablation of any type of specific cell population, Molecular reproduction and Development, 72(1):54-67 (2005).
Shah et al., "Double-inducible gene activation system for caspase 3 and 9 in epidermis," Genesis: The Journal of Genetics and Development, 45(4):194-199 (2007).
Shiozaki et al., "Regulation of Initiator Caspase Activity," Sci. STKE 2003(172):tw95 (2003) (Abstract Only).
Trujillo et al., "Apoptosis through targeted activation of caspase 8 ("ATTAC-mice"): novel mouse models of inducible and reversible tissue ablation," Cell Cycle, 4(9):1141-1145 (2005).
Written Opinion of the International Seaching Authority for International Application No. PCT/US09/30780, dated Apr. 10, 2009.

* cited by examiner plasmid: pCMVfloxMFv2Casp3E  size: 9,912bp 230-816 CMV promoter
861-880 T7 promoter
899-932 loxH
953-4009 LacZ
4022-4063 V5 epitope
4073-4089 6xHis
4171-4379 BGH polyA
4386-4416 loxP 4504-6075 MFv2Casp3E
  4504-4548 myrstoylation signal
  4551-4875 FKBP
  4876-5210 FKBP
  5211-6039 Caspase3 element
  6040-6075 HA-tag
6157-6383 BGH polyA
8916-9776 Ampicillin resist

Figure 3A pC4M-Fv2E Annotated Sequence - SEQ ID NO:2

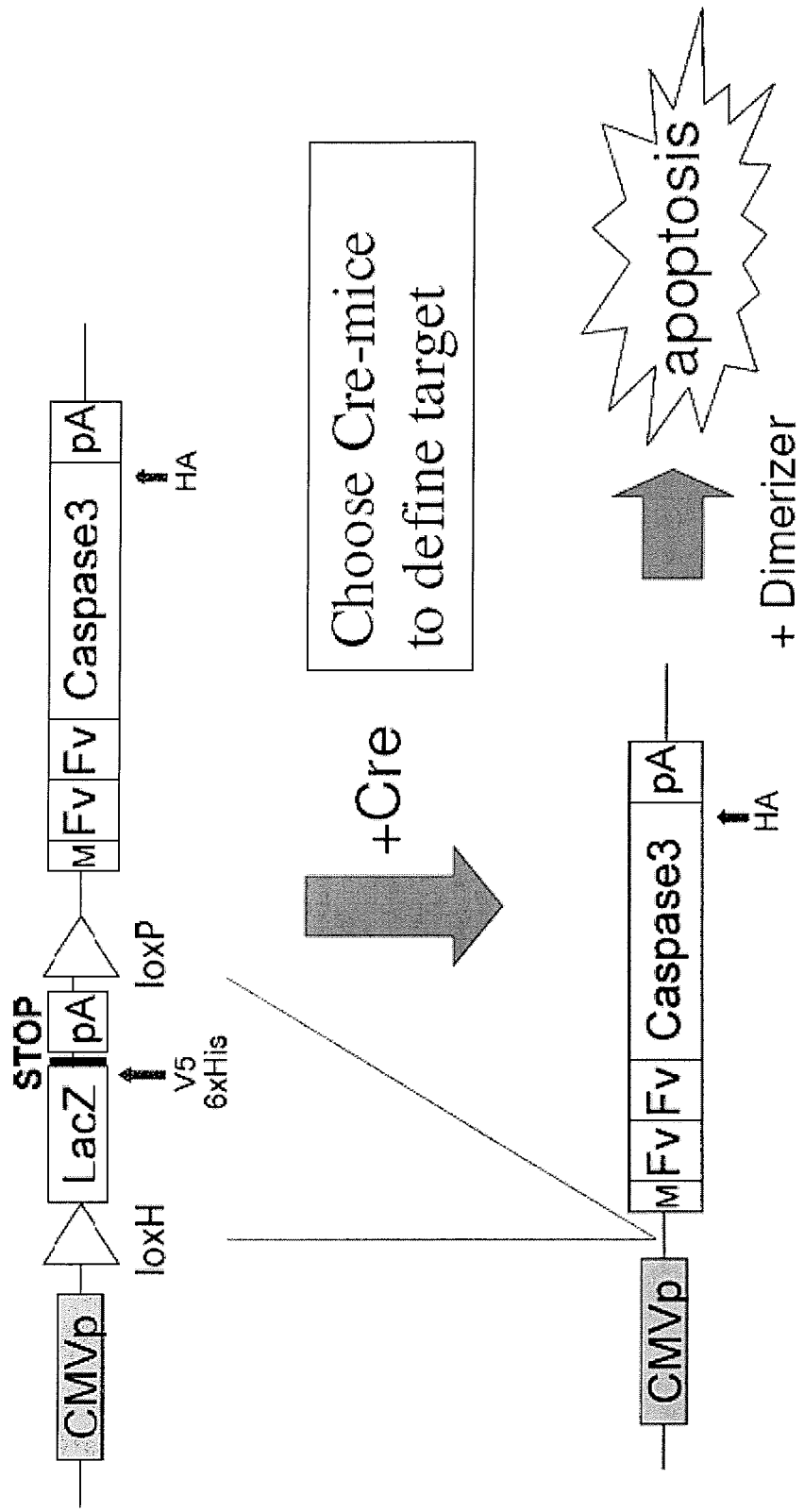

Figure 6A
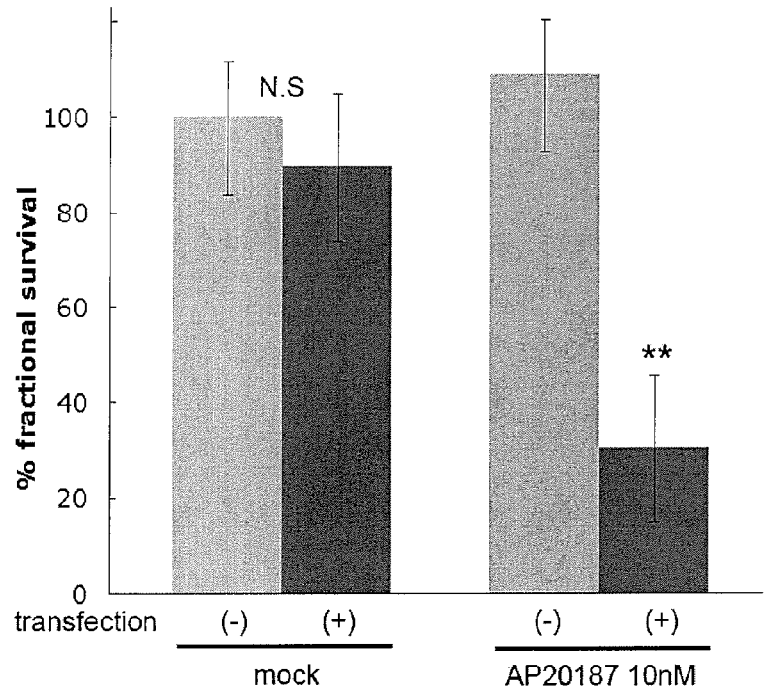
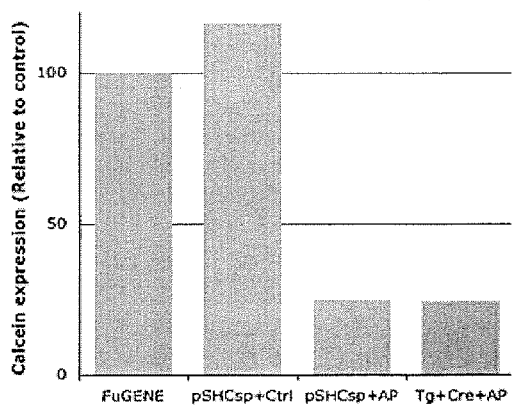
Figure 6B
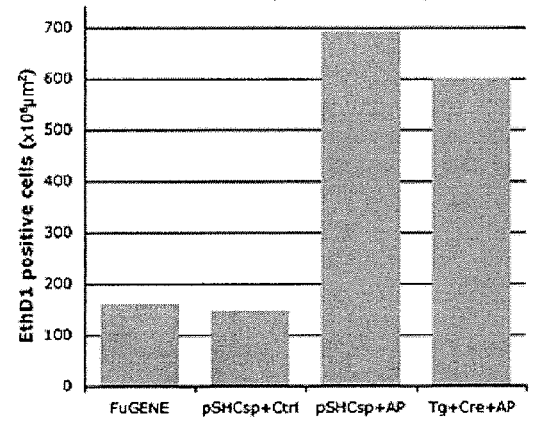
Figure 6C

Figure 7

| Transgenic Line | A | B | C | D | E | F | G |
|---|---|---|---|---|---|---|---|
| 1) F1-genotyping: to check the transgene inserted | + | + | + | + | - | + | - |
| 2) F1-LacZ embryo: to check the protein distribution | - | + | - | + | - | + | |
| 3) F1-whole body expression in adult: to see detailed organ specific protein distribution in adult | - | + | - | + | - | + | |

Figure 8B
Cre (+)
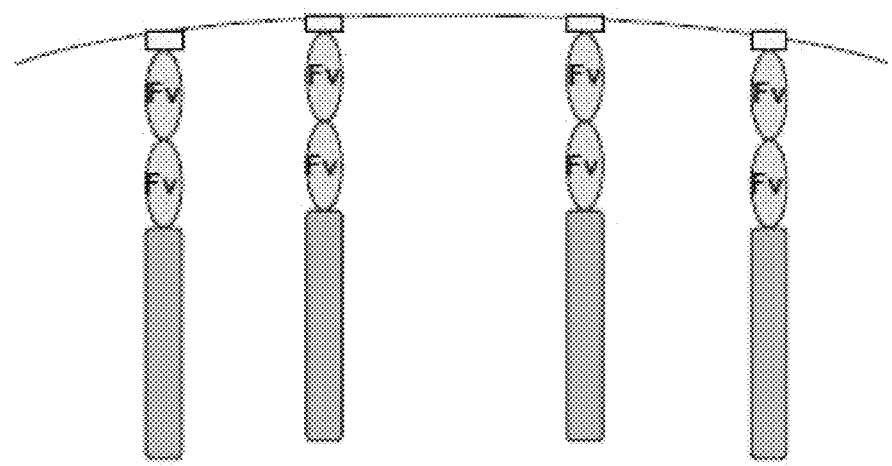
(absence of LacZ)
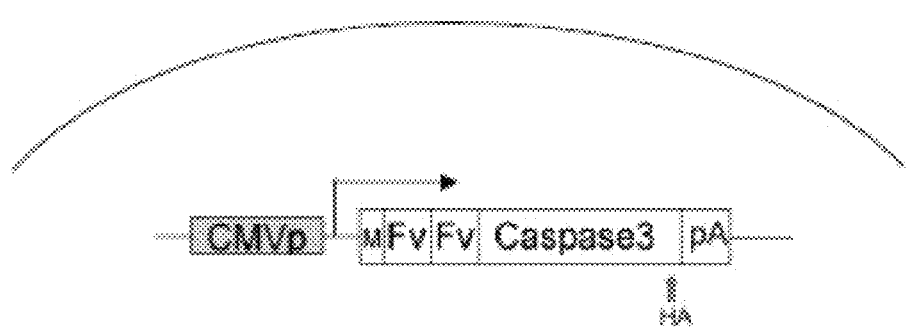

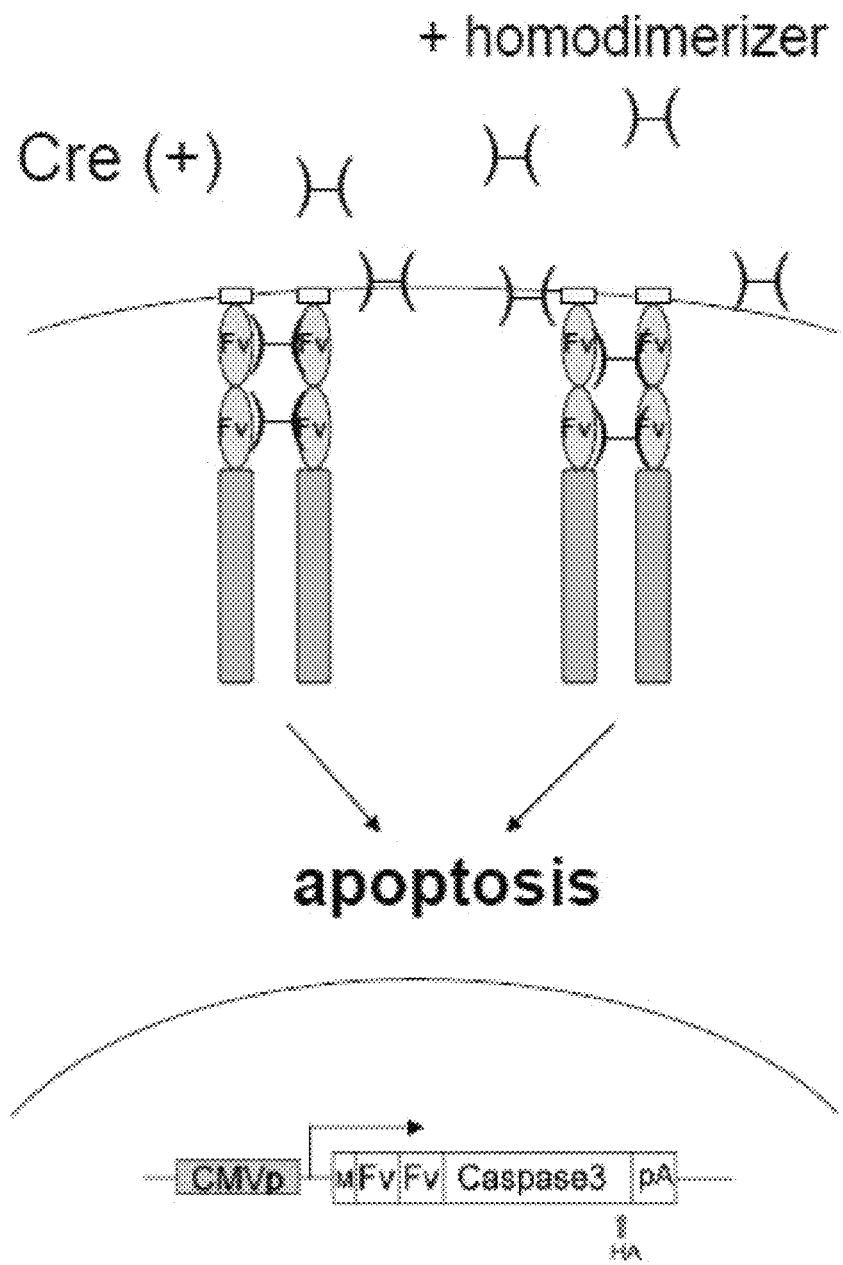

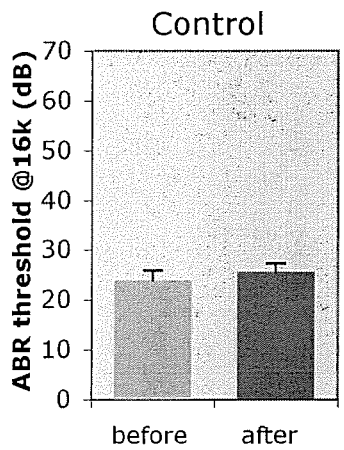
Figure 9A Control
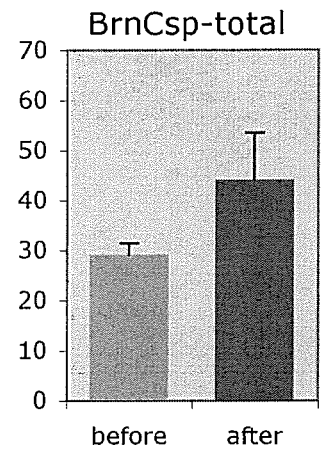
Figure 9B BrnCsp-total
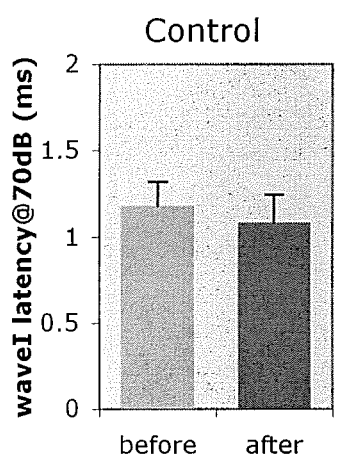
Figure 9C Control
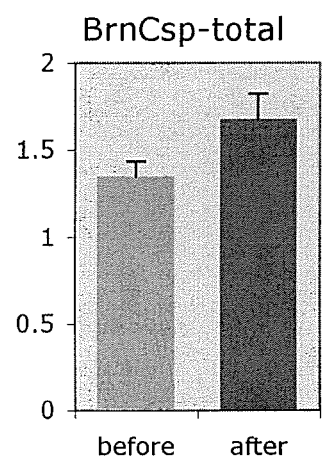
Figure 9D BrnCsp-total
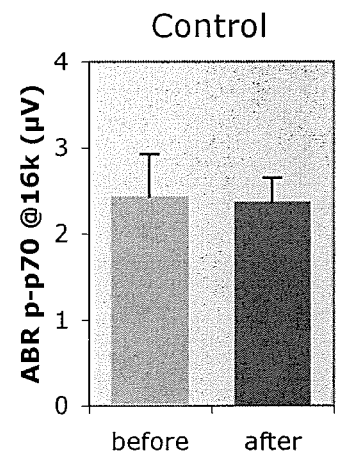
Figure 9E Control
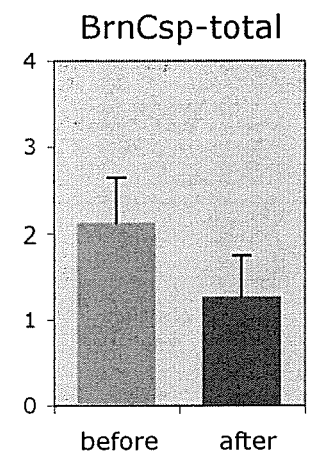
Figure 9F BrnCsp-total Figure 11A
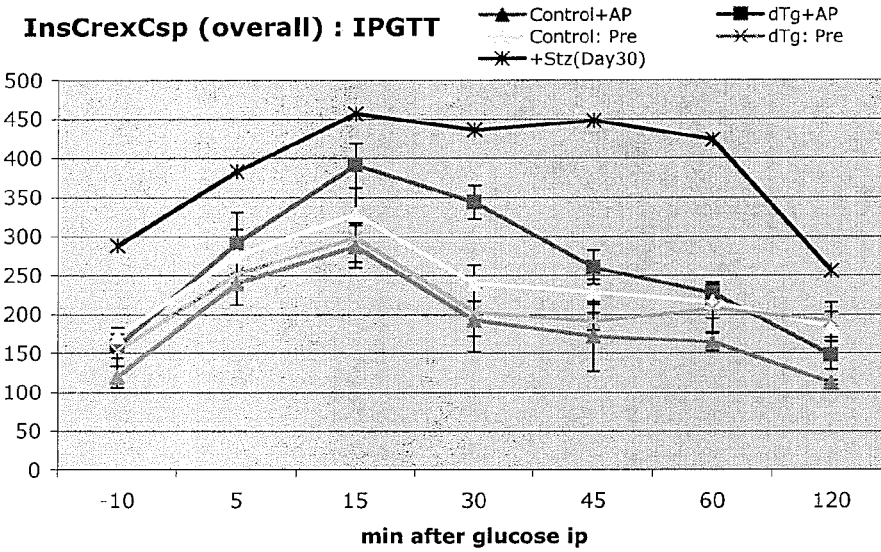
Figure 11B
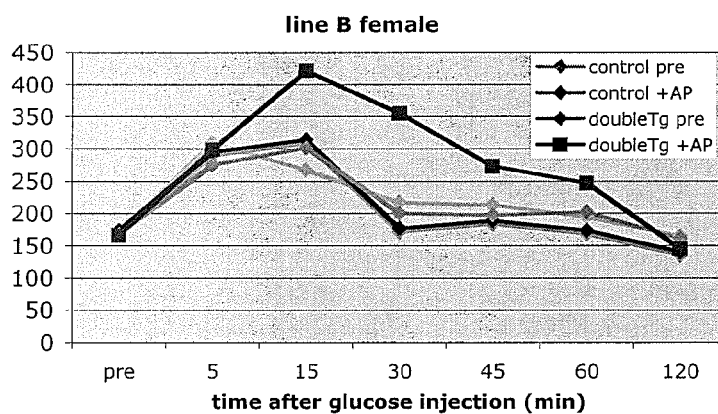
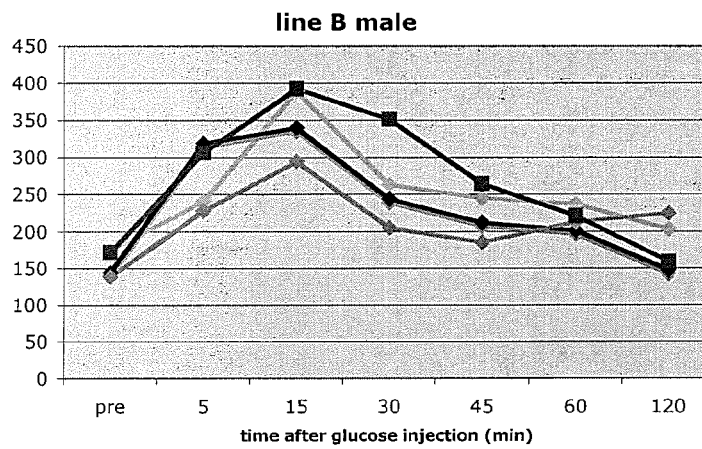
Figure 11C

SEQUENCE LISTING

<160> NUMBER OF SEQ ID NOS: 19

<210> SEQ ID NO 1
<211> LENGTH: 19824
<212> TYPE: DNA
<213> ORGANISM: Artificial Sequence
<220> FEATURE:
<223> OTHER INFORMATION: Synthetic construct

<400> SEQUENCE: 1

```
gttaattaag gatctcccga tcccctatgg tgcactctca gtacaatctg ctctgatgcc      60
gcatagttaa gccagtatct gctccctgct tgtgtgttgg aggtcgctga gtagtgcgcg     120
agcaaaattt aagctacaac aaggcaaggc ttgaccgaca attgcatgaa gaatctgctt     180
agggttaggc gttttgcgct gcttcgcgat gtacgggcca gatatacgcg ttgacattga     240
ttattgacta gttattaata gtaatcaatt acgggtcat tagttcatag cccatatatg      300
gagttccgcg ttacataact tacggtaaat ggcccgcctg gctgaccgcc caacgacccc     360
cgcccattga cgtcaataat gacgtatgtt cccatagtaa cgccaatagg gactttccat     420
tgacgtcaat gggtggagta tttacggtaa actgcccact tggcagtaca tcaagtgtat     480
catatgccaa gtacgccccc tattgacgtc aatgacggta aatggcccgc ctggcattat     540
gcccagtaca tgaccttatg gactttcct acttggcagt acatctacgt attagtcatc      600
gctattacca tggtgatgcg gttttggcag tacatcaatg ggcgtggata gcggtttgac     660
tcacggggat ttccaagtct ccaccccatt gacgtcaatg ggagtttgtt ttggcaccaa     720
aatcaacggg actttccaaa atgtcgtaac aactccgccc cattgacgca aatgggcggt     780
aggcgtgtac ggtgggaggt ctatataagc agagctctct ggctaactag agaacccact     840
gcttactggc ttatcgaaat taatacgact cactataggg agacccaagc tggctagaat     900
tacctcatat agcatacatt atacgaagtt atcggaggaa ttcgccctta ccatggttga     960
tcccgtcgtt ttacaacgtc gtgactggga aaaccctggc gttacccaac ttaatcgcct    1020
tgcagcacat cccccttcg ccagctggcg taatagcgaa gaggcccgca ccgatcgccc     1080
ttcccaacag ttgcgcagcc tgaatggcga atggcgcttt gcctggtttc cggcaccaga    1140
agcggtgccg gaaagctggc tggagtgcga tcttcctgag gccgatactg tcgtcgtccc    1200
ctcaaactgg cagatgcacg gttacgatgc gcccatctac accaacgtaa cctatcccat    1260
tacggtcaat ccgccgtttg ttcccacgga gaatccgacg ggttgttact cgctcacatt    1320
taatgttgat gaaagctggc tacaggaagg ccagacgcga attattttg atggcgttaa     1380
ctcggcgttt catctgtggt gcaacgggcg ctgggtcgt tacggccagg acagtcgttt     1440
gccgtctgaa tttgacctga gcgcattttt acgcgccgga gaaaaccgcc tcgcggtgat    1500
ggtgctgcgt tggagtgacg gcagttatct ggaagatcag gatatgtggc ggatgagcgg    1560
cattttccgt gacgtctcgt tgctgcataa accgactaca caaatcagcg atttccatgt    1620
tgccactcgc tttaatgatg atttcagccg cgctgtactg gaggctgaag ttcagatgtg    1680
cggcgagttg cgtgactacc tacgggtaac agtttcttta tggcagggtg aaacgcaggt    1740
cgccagcggc accgcgcctt tcggcggtga aattatcgat gagcgtggtg gttatgccga    1800
tcgcgtcaca ctacgtctga acgtcgaaaa cccgaaactg tggagcgccg aaatcccgaa    1860
tctctatcgt gcggtggttg aactgcacac cgccgacgc acgctgattg aagcagaagc    1920
ctgcgatgtc ggtttccgcg aggtgcggat tgaaaatggt ctgctgctgc tgaacggcaa    1980
gccgttgctg attcgaggcg ttaaccgtca cgagcatcat cctctgcatg gtcaggtcat    2040
```

```
ggatgagcag acgatggtgc aggatatcct gctgatgaag cagaacaact ttaacgccgt    2100
gcgctgttcg cattatccga accatccgct gtggtacacg ctgtgcgacc gctacggcct    2160
gtatgtggtg gatgaagcca atattgaaac ccacggcatg gtgccaatga atcgtctgac    2220
cgatgatccg cgctggctac cggcgatgag cgaacgcgta acgcgaatgg tgcagcgcga    2280
tcgtaatcac ccgagtgtga tcatctggtc gctggggaat gaatcaggcc acggcgctaa    2340
tcacgacgcg ctgtatcgct ggatcaaatc tgtcgatcct tcccgcccgg tgcagtatga    2400
aggcggcgga gccgacacca cggccaccga tattatttgc ccgatgtacg cgcgcgtgga    2460
tgaagaccag cccttcccgg ctgtgccgaa atggtccatc aaaaaatggc tttcgctacc    2520
tggagagacg cgcccgctga tcctttgcga atacgcccac gcgatgggta acagtcttgg    2580
cggtttcgct aaatactggc aggcgtttcg tcagtatccc cgtttacagg gcggcttcgt    2640
ctgggactgg gtggatcagt cgctgattaa atatgatgaa aacggcaacc cgtggtcggc    2700
ttacggcggt gattttggcg atacgccgaa cgatcgccag ttctgtatga acggtctggt    2760
ctttgccgac cgcacgccgc atccagcgct gacggaagca aaacaccagc agcagttttt    2820
ccagttccgt ttatccgggc aaaccatcga agtgaccagc gaatacctgt tccgtcatag    2880
cgataacgag ctcctgcact ggatggtggc gctggatggt aagccgctgg caagcggtga    2940
agtgcctctg gatgtcgctc cacaaggtaa acagttgatt gaactgcctg aactaccgca    3000
gccggagagc gccgggcaac tctggctcac agtacgcgta gtgcaaccga acgcgaccgc    3060
atggtcagaa gccgggcaca tcagcgcctg gcagcagtgg cgtctggcgg aaaacctcag    3120
tgtgacgctc cccgccgcgt cccacgccat cccgcatctg accaccagcg aaatggattt    3180
ttgcatcgag ctgggtaata agcgttggca atttaaccgc cagtcaggct ttctttcaca    3240
gatgtggatt ggcgataaaa acaactgct gacgccgctg cgcgatcagt tcacccgtgc    3300
accgctggat aacgacattg gcgtaagtga agcgacccgc attgacccta acgcctgggt    3360
cgaacgctgg aaggcggcgg gccattacca ggccgaagca gcgttgttgc agtgcacggc    3420
agatacactt gctgatgcgg tgctgattac gaccgctcac gcgtggcagc atcaggggaa    3480
aaccttattt atcagccgga aaacctaccg gattgatggt agtggtcaaa tggcgattac    3540
cgttgatgtt gaagtggcga gcgatacacc gcatccggcg cggattggcc tgaactgcca    3600
gctggcgcag gtagcagagc gggtaaactg gctcggatta gggccgcaag aaaactatcc    3660
cgaccgcctt actgccgcct gttttgaccg ctgggatctg ccattgtcag acatgtatac    3720
cccgtacgtc ttcccgagcg aaaacggtct gcgctgcggg acgcgcgaat tgaattatgg    3780
cccacaccag tggcgcggcg acttccagtt caacatcagc cgctacagtc aacagcaact    3840
gatggaaacc agccatcgcc atctgctgca cgcggaagaa ggcacatggc tgaatatcga    3900
cggtttccat atggggattg gtggcgacga ctcctggagc ccgtcagtat cggcggaatt    3960
ccagctgagc gccggtcgct accattacca gttggtctgg tgtcaaaaaa agggcgaatt    4020
cggtaagcct atccctaacc ctctcctcgg tctcgattct acgcgtaccg gtcatcatca    4080
ccatcaccat tgactcgaga acatatggcc atgggatcc gcggccgcaa ttgttaacag    4140
atccgtcgac gagctcgcta tcagcctcga ctgtgccttc tagttgccag ccatctgttg    4200
tttgcccctc cccgtgcct tccttgaccc tggaaggtgc cactcccact gtcctttcct    4260
aataaaatga ggaaattgca tcgcattgtc tgagtaggtg tcattctatt ctggggggtg    4320
gggtggggca ggacagcaag ggggaggatt gggaagacaa tagcaggcat gctggggatt    4380
```

```
ctagtataac ttcgtatagc atacattata cgaagttata agctggctag cgtttaaact    4440
taagcttggt accacgcatg ctgcagacgc gttacgtatc ggatccagaa ttcgtgatcc    4500
accatgggga gtagcaagag caagcctaag gaccccagcc agcgcctcga gggagtgcag    4560
gtggagacta tctccccagg agacgggcgc accttcccca agcgcggcca gacctgcgtg    4620
gtgcactaca ccgggatgct tgaagatgga aagaaagttg attcctcccg ggacagaaac    4680
aagcccttta agtttatgct aggcaagcag gaggtgatcc gaggctggga agaaggggtt    4740
gcccagatga gtgtgggtca gagagccaaa ctgactatat ctccagatta tgcctatggt    4800
gccactgggc acccaggcat catcccacca catgccactc tcgtcttcga tgtggagctt    4860
ctaaaactgg aagtcgaggg agtgcaggtg gagactatct ccccaggaga cgggcgcacc    4920
ttccccaagc gcggccagac ctgcgtggtg cactacaccg ggatgcttga agatggaaag    4980
aaagttgatt cctcccggga cagaaacaag ccctttaagt ttatgctagg caagcaggag    5040
gtgatccgag gctgggaaga aggggttgcc cagatgagtg tgggtcagag agccaaactg    5100
actatatctc cagattatgc ctatggtgcc actgggcacc caggcatcat cccaccacat    5160
gccactctcg tcttcgatgt ggagcttcta aaactggaag tcgaggagaa cactgaaaac    5220
tcagtggatt caaaatccat taaaaatttg aaccaaaga tcatacatgg aagcgaatca    5280
atggactctg aatatcccct ggacaacagt tataaaatgg attatcctga tgggttta    5340 tgtataataa ttaataataa gaattttcat aaaagcactg gaatgacatc tcggtctggt    5400
acagatgtcg atgcagcaaa cctcagggaa acattcagaa acttgaaata tgaagtcagg    5460
aataaaaatg atcttacacg tgaagaaatt gtggaattga tgcgtgatgt ttctaaagaa    5520
gatcacagca aaaggagcag ttttgtttgt gtgcttctga gccatggtga agaaggaata    5580
attttttgga acaaatggacc tgttgacctg aaaaaaataa caaactttt cagagggat    5640 cgttgtagaa gtctaactgg aaaacccaaa cttttcatta ttcaggcctg ccgtggtaca    5700
gaactggact gtggcattga cagacagt ggtgttgatg atgacatggc gtgtcataaa    5760
ataccagtgg aggccgactt cttgtatgca tactccacag cacctggtta ttattcttgg    5820
cgaaattcaa aggatggctc ctggttcatc cagtcgcttt tgtgccatgct gaaacagtat    5880 gccgacaagc ttgaatttat gcacattctt acccgggtta accgaaaggt ggcaacagaa    5940
tttgagtcct tttcctttga cgctactttt catgcaaaga aacagattcc atgtattgtt    6000
tccatgctca caaaagaact ctatttttat cacgtcgact atccgtacga cgtaccagac    6060
tacgcactcg actaagaatt ccatctgaat tcgtcgacaa gcttctcgag cctaggctag    6120
ctctagaggg cccgtttaaa cccgctgatc agcctcgact gtgccttcta gttgccagcc    6180
atctgttgtt tgcccctccc ccgtgccttc cttgaccctg gaaggtgcca ctcccactgt    6240
cctttcctaa taaaatgagg aaattgcatc gcattgtctg agtaggtgtc attctattct    6300
ggggggtggg gtggggcagg acagcaaggg ggaggattgg gaagacaata gcaggcatgc    6360
tggggatgcg gtgggctcta tggcttctga ggcggaaaga acttaattaa ctagctagaa    6420
gatccggctg ctaacaaagc ccgaaaggaa gctgagttgg ctgctgccac cgctgagcaa    6480
taactagcat aaccccttgg ggcctctaaa cgggtcttga gggttttttt gctgaaagga    6540
ggaactatat ccggatatcc cgggagcttg tatatccatt ttcggatctg atcaagagac    6600
aggatgagga tcgtttcgca tgattgaaca agatggattg cacgcaggtt ctccggccgc    6660
ttgggtggag aggctattcg gctatgactg ggcacaacag acaatcggct gctctgatgc    6720
cgccgtgttc cggctgtcag cgcaggggcg cccggttctt tttgtcaaga ccgacctgtc    6780
```

```
cggtgccctg aatgaactgc aggacgaggc agcgcggcta tcgtggctgg ccacgacggg    6840
cgttccttgc gcagctgtgc tcgacgttgt cactgaagcg ggaagggact ggctgctatt    6900
gggcgaagtg ccggggcagg atctcctgtc atctcacctt gctcctgccg agaaagtatc    6960
catcatggct gatgcaatgc ggcggctgca tacgcttgat ccggctacct gcccattcga    7020
ccaccaagcg aaacatcgca tcgagcgagc acgtactcgg atggaagccg gtcttgtcga    7080
tcaggatgat ctggacgaag agcatcaggg gctcgcgcca gccgaactgt tcgccaggct    7140
caaggcgcgc atgcccgacg gcgaggatct cgtcgtgacc catggcgatg cctgcttgcc    7200
gaatatcatg gtggaaaatg gccgcttttc tggattcatc gactgtggcc ggctgggtgt    7260
ggcggaccgc tatcaggaca tagcgttggc tacccgtgat attgctgaag agcttggcgg    7320
cgaatgggct gaccgcttcc tcgtgcttta cggtatcgcc gctcccgatt cgcagcgcat    7380
cgccttctat cgccttcttg acgagttctt ctgagcggga ctctggggtt cgaaatgacc    7440
gaccaagcga cgcccaacct gccatcacga gatttcgatt ccaccgccgc cttctatgaa    7500
aggttgggct tcggaatcgt tttccgggac gccggctgga tgatcctcca gcgcggggat    7560
ctcatgctgg agttcttcgc ccaccccaac ttgtttattg cagcttataa tggttacaaa    7620
taaagcaata gcatcacaaa tttcacaaat aaagcatttt tttcactgca ttctagttgt    7680
ggtttgtcca aactcatcaa tgtatcttat catgtctgta taccgtcgac tctagctag    7740 agcttggcgt aatcatggtc atagctgttt cctgtgtgaa attgttatcc gctcacaatt    7800
ccacacaaca tacgagccgg aagcataaag tgtaaagcct ggggtgccta atgagtgagc    7860
taactcacat taattgcgtt gcgctcactg cccgctttcc agtcgggaaa cctgtcgtgc    7920
cagctgcatt aatgaatcgg ccaacgcgcg gggagaggcg gtttgcgtat tgggcgctct    7980
tccgcttcct cgctcactga ctcgctgcgc tcggtcgttc ggctgcggcg agcggtatca    8040
gctcactcaa aggcggtaat acggttatcc acagaatcag gggataacgc aggaaagaac    8100
atgtgagcaa aaggccagca aaaggccagg aaccgtaaaa aggccgcgtt gctggcgttt    8160
ttccataggc tccgcccccc tgacgagcat cacaaaaatc gacgctcaag tcagaggtgg    8220
cgaaacccga caggactata aagataccag gcgtttcccc ctggaagctc cctcgtgcgc    8280
tctcctgttc cgaccctgcc gcttaccgga tacctgtccg cctttctccc ttcgggaagc    8340
gtggcgcttt ctcatagctc acgctgtagg tatctcagtt cggtgtaggt cgttcgctcc    8400
aagctgggct gtgtgcacga accccccgtt cagcccgacc gctgcgcctt atccggtaac    8460
tatcgtcttg agtccaaccc ggtaagacac gacttatcgc cactggcagc agccactggt    8520
aacaggatta gcagagcgag gtatgtaggc ggtgctacag agttcttgaa gtggtggcct    8580
aactacggct acactagaag aacagtattt ggtatctgcg ctctgctgaa gccagttacc    8640
ttcggaaaaa gagttggtag ctcttgatcc ggcaaacaaa ccaccgctgg tagcggtttt    8700
tttgtttgca agcagcagat tacgcgcaga aaaaaaggat ctcaagaaga tcctttgatc    8760
ttttctacgg ggtctgacgc tcagtggaac gaaaactcac gttaagggat tttggtcatg    8820
agattatcaa aaaggatctt cacctagatc cttttaaatt aaaaatgaag ttttaaatca    8880
atctaaagta tatatgagta aacttggtct gacagttacc aatgcttaat cagtgaggca    8940
cctatctcag cgatctgtct atttcgttca tccatagttg cctgactccc cgtcgtgtag    9000
ataactacga tacgggaggg cttaccatct ggccccagtg ctgcaatgat accgcgagac    9060
ccacgctcac cggctccaga tttatcagca ataaaccagc cagccggaag ggccgagcgc    9120
```

-continued

```
agaagtggtc ctgcaacttt atccgcctcc atccagtcta ttaattgttg ccgggaagct   9180
agagtaagta gttcgccagt taatagtttg cgcaacgttg ttgccattgc tacaggcatc   9240
gtggtgtcac gctcgtcgtt tggtatggct tcattcagct ccggttccca acgatcaagg   9300
cgagttacat gatcccccat gttgtgcaaa aaagcggtta gctccttcgg tcctccgatc   9360
gttgtcagaa gtaagttggc cgcagtgtta tcactcatgg ttatggcagc actgcataat   9420
tctcttactg tcatgccatc cgtaagatgc ttttctgtga ctggtgagta ctcaaccaag   9480
tcattctgag aatagtgtat gcggcgaccg agttgctctt gcccggcgtc aatacgggat   9540
aataccgcgc cacatagcag aactttaaaa gtgctcatca ttggaaaacg ttcttcgggg   9600
cgaaaactct caaggatctt accgctgttg agatccagtt cgatgtaacc cactcgtgca   9660
cccaactgat cttcagcatc ttttactttc accagcgttt ctgggtgagc aaaaacagga   9720
aggcaaaatg ccgcaaaaaa gggaataagg gcgacacgga aatgttgaat actcatactc   9780
ttccttttc aatattattg aagcatttat cagggttatt gtctcatgag cggatacata   9840
tttgaatgta tttagaaaaa taaacaaata ggggttccgc gcacatttcc ccgaaaagtg   9900
ccacctgacg tcgttaatta aggatctccc gatccctat ggtgcactct cagtacaatc   9960
tgctctgatg ccgcatagtt aagccagtat ctgctccctg cttgtgtgtt ggaggtcgct  10020
gagtagtgcg cgagcaaaat ttaagctaca acaaggcaag gcttgaccga caattgcatg  10080
aagaatctgc ttagggttag gcgttttgcg ctgcttcgcg atgtacgggc cagatatacg  10140
cgttgacatt gattattgac tagttattaa tagtaatcaa ttacggggtc attagttcat  10200
agcccatata tggagttccg cgttacataa cttacggtaa atggcccgcc tggctgaccg  10260
cccaacgacc cccgcccatt gacgtcaata atgacgtatg ttcccatagt aacgccaata  10320
gggactttcc attgacgtca atgggtggag tatttacggt aaactgccca cttggcagta  10380
catcaagtgt atcatatgcc aagtacgccc cctattgacg tcaatgacgg taaatggccc  10440
gcctggcatt atgcccagta catgacctta tgggactttc ctacttggca gtacatctac  10500
gtattagtca tcgctattac catggtgatg cggttttggc agtacatcaa tgggcgtgga  10560
tagcggtttg actcacgggg atttccaagt ctccacccca ttgacgtcaa tgggagtttg  10620
ttttggcacc aaaatcaacg ggactttcca aaatgtcgta caactccgc cccattgacg  10680
caaatgggcg gtaggcgtgt acggtgggag gtctatataa gcagagctct ctggctaact  10740
agagaaccca ctgcttactg gcttatcgaa attaatacga ctcactatag ggagacccaa  10800
gctggctaga attacctcat atagcataca ttatacgaag ttatcggagg aattcgccct  10860
taccatggtt gatcccgtcg ttttacaacg tcgtgactgg gaaaaccctg gcgttaccca  10920
acttaatcgc cttgcagcac atccccttt cgccagctgg cgtaatagcg aagaggcccg  10980
caccgatcgc ccttcccaac agttgcgcag cctgaatggc gaatggcgct ttgcctggtt  11040
tccggcacca gaagcggtgc cggaaagctg gctggagtgc gatcttcctg aggccgatac  11100
tgtcgtcgtc ccctcaaact ggcagatgca cggttacgat gcgcccatct acaccaacgt  11160
aacctatccc attacggtca atccgccgtt tgttcccacg gagaatccga cgggttgtta  11220
ctcgctcaca tttaatgttg atgaaagctg gctacaggaa ggccagacgc gaattatttt  11280
tgatggcgtt aactcggcgt ttcatctgtg gtgcaacggg cgctgggtcg gttacggcca  11340
ggacagtcgt ttgccgtctg aatttgacct gagcgcattt ttacgcgccg gagaaaaccg  11400
cctcgcggtg atggtgctgc gttggagtga cggcagttat ctggaagatc aggatatgtg  11460
gcggatgagc ggcattttcc gtgacgtctc gttgctgcat aaaccgacta cacaaatcag  11520
```

```
cgatttccat gttgccactc gctttaatga tgatttcagc cgcgctgtac tggaggctga   11580
agttcagatg tgcggcgagt tgcgtgacta cctacgggta acagtttctt tatggcaggg   11640
tgaaacgcag gtcgccagcg gcaccgcgcc tttcggcggt gaaattatcg atgagcgtgg   11700
tggttatgcc gatcgcgtca cactacgtct gaacgtcgaa aacccgaaac tgtggagcgc   11760
cgaaatcccg aatctctatc gtgcggtggt tgaactgcac accgccgacg gcacgctgat   11820
tgaagcagaa gcctgcgatg tcggtttccg cgaggtgcgg attgaaaatg gtctgctgct   11880
gctgaacggc aagccgttgc tgattcgagg cgttaaccgt cacgagcatc atcctctgca   11940
tggtcaggtc atggatgagc agacgatggt gcaggatatc ctgctgatga agcagaacaa   12000
ctttaacgcc gtgcgctgtt cgcattatcc gaaccatccg ctgtggtaca cgctgtgcga   12060
ccgctacggc ctgtatgtgg tggatgaagc caatattgaa acccacggca tggtgccaat   12120
gaatcgtctg accgatgatc cgcgctggct accggcgatg agcgaacgcg taacgcgaat   12180
ggtgcagcgc gatcgtaatc acccgagtgt gatcatctgg tcgctgggga atgaatcagg   12240
ccacggcgct aatcacgacg cgctgtatcg ctggatcaaa tctgtcgatc cttcccgccc   12300
ggtgcagtat gaaggcggcg gagccgacac cacggccacc gatattattt gcccgatgta   12360
cgcgcgcgtg gatgaagacc agcccttccc ggctgtgccg aaatggtcca tcaaaaaatg   12420
gctttcgcta cctggagaga cgcgcccgct gatcctttgc gaatacgccc acgcgatggg   12480
taacagtctt ggcggtttcg ctaaatactg gcaggcgttt cgtcagtatc cccgtttaca   12540
gggcggcttc gtctgggact gggtggatca gtcgctgatt aaatatgatg aaaacggcaa   12600
cccgtggtcg gcttacggcg gtgattttgg cgatacgccg aacgatcgcc agttctgtat   12660
gaacggtctg gtctttgccg accgcacgcc gcatccagcg ctgacggaag caaaacacca   12720
gcagcagttt ttccagttcc gtttatccgg gcaaaccatc gaagtgacca gcgaatacct   12780
gttccgtcat agcgataacg agctcctgca ctggatggtg gcgctggatg gtaagccgct   12840
ggcaagcggt gaagtgcctc tggatgtcgc tccacaaggt aaacagttga ttgaactgcc   12900
tgaactaccg cagccggaga gcgccgggca actctggctc acagtacgcg tagtgcaacc   12960
gaacgcgacc gcatggtcag aagccgggca catcagcgcc tggcagcagt ggcgtctggc   13020
ggaaaacctc agtgtgacgc tccccgccgc gtcccacgcc atcccgcatc tgaccaccag   13080
cgaaatggat ttttgcatcg agctgggtaa taagcgttgg caatttaacc gccagtcagg   13140
ctttctttca cagatgtgga ttggcgataa aaaacaactg ctgacgccgc tgcgcgatca   13200
gttcacccgt gcaccgctgg ataacgacat tggcgtaagt gaagcgaccc gcattgaccc   13260
taacgcctgg gtcgaacgct ggaaggcggc gggccattac caggccgaag cagcgttgtt   13320
gcagtgcacg gcagatacac ttgctgatgc ggtgctgatt acgaccgctc acgcgtggca   13380
gcatcagggg aaaaccttat ttatcagccg gaaaacctac cggattgatg gtagtggtca   13440
aatggcgatt accgttgatg ttgaagtggc gagcgataca ccgcatccgg cgcggattgg   13500
cctgaactgc cagctggcgc aggtagcaga gcgggtaaac tggctcggat tagggccgca   13560 agaaaaactat cccgaccgcc ttactgccgc ctgttttgac cgctgggatc tgccattgtc   13620
agacatgtat accccgtacg tcttcccgag cgaaaacggt ctgcgctgcg ggacgcgcga   13680
attgaattat ggcccacacc agtggcgcgg cgacttccag ttcaacatca gccgctacag   13740
tcaacagcaa ctgatggaaa ccagccatcg ccatctgctg cacgcggaag aaggcacatg   13800
gctgaatatc gacggttttcc atatggggat tggtggcgac gactcctgga gcccgtcagt   13860
```

```
atcggcggaa ttccagctga gcgccggtcg ctaccattac cagttggtct ggtgtcaaaa   13920
aaagggcgaa ttcggtaagc ctatccctaa ccctctcctc ggtctcgatt ctacgcgtac   13980
cggtcatcat caccatcacc attgactcga gaacatatgg ccatggggat ccgcggccgc   14040
aattgttaac agatccgtcg acgagctcgc tatcagcctc gactgtgcct tctagttgcc   14100
agccatctgt tgtttgcccc tcccccgtgc cttccttgac cctggaaggt gccactccca   14160
ctgtcctttc ctaataaaat gaggaaattg catcgcattg tctgagtagg tgtcattcta   14220
ttctgggggg tggggtgggg caggacagca agggggagga ttgggaagac aatagcaggc   14280
atgctgggga ttctagtata acttcgtata gcatacatta tacgaagtta taagctggct   14340 agcgttaaa cttaagcttg gtaccacgca tgctgcagac gcgttacgta tcggatccag   14400
aattcgtgat ccaccatggg gagtagcaag agcaagccta aggacccag ccagcgcctc   14460 gagggagtgc aggtggagac tatctcccca ggagacgggc gcaccttccc caagcgcggc   14520
cagacctgcg tggtgcacta caccgggatg cttgaagatg gaagaaagt tgattcctcc   14580 cgggacagaa acaagcccct taagtttatg ctaggcaagc aggaggtgat ccgaggctgg   14640
gaagaagggg ttgcccagat gagtgtgggt cagagagcca aactgactat atctccagat   14700
tatgcctatg gtgccactgg gcacccaggc atcatcccac cacatgccac tctcgtcttc   14760
gatgtggagc ttctaaaact ggaagtcgag ggagtgcagg tggagactat ctccccagga   14820
gacgggcgca ccttccccaa gcgcggccag acctgcgtgg tgcactacac cgggatgctt   14880
gaagatggaa agaaagttga ttcctcccgg gacagaaaca gccctttaa gtttatgcta   14940 ggcaagcagg aggtgatccg aggctgggaa gaggggttg cccagatgag tgtgggtcag   15000
agagccaaac tgactatatc tccagattat gcctatggtg ccactgggca cccaggcatc   15060
atcccaccac atgccactct cgtcttcgat gtggagcttc taaaactgga agtcgaggag   15120
aacactgaaa actcagtgga ttcaaaatcc attaaaaatt tggaaccaaa gatcatacat   15180
ggaagcgaat caatggactc tggaatatcc ctggacaaca gttataaaat ggattatcct   15240
gagatgggtt tatgtataat aattaataat aagaattttc ataaaagcac tggaatgaca   15300
tctcggtctg gtacagatgt cgatgcagca acctcagggg aaacattcag aaacttgaaa   15360
tatgaagtca ggaataaaaa tgatcttaca cgtgaagaaa ttgtggaatt gatgcgtgat   15420
gtttctaaag aagatcacag caaaaggagc agttttgttt gtgtgcttct gagccatggt   15480
gaagaaggaa taatttttgg aacaaatgga cctgttgacc tgaaaaaat aacaaacttt   15540 ttcagagggg atcgttgtag aagtctaact ggaaaaccca aacttttcat tattcaggcc   15600
tgccgtggta cagaactgga ctgtggcatt gagacagaca gtggtgttga tgatgacatg   15660
gcgtgtcata aaataccagt ggaggccgac ttcttgtatg catactccac agcacctggt   15720
tattattctt ggcgaaattc aaaggatggc tcctggttca tccagtcgct ttgtgccatg   15780
ctgaaacagt atgccgacaa gcttgaattt atgcacattc ttacccgggt taaccgaaag   15840
gtggcaacag aatttgagtc ctttttcctt gacgctactt ttcatgcaaa gaaacagatt   15900
ccatgtattg tttccatgct cacaaaagaa ctctattttt atcacgtcga ctatccgtac   15960
gacgtaccag actacgcact cgactaagaa ttccatctga attcgtcgac aagcttctcg   16020
agcctaggct agctctagag ggcccgttta aacccgctga tcagcctcga ctgtgccttc   16080
tagttgccag ccatctgttg tttgcccctc ccccgtgcct tccttgaccc tggaaggtgc   16140
cactcccact gtccttttcct aataaaatga ggaaattgca tcgcattgtc tgagtaggtg   16200
tcattctatt ctgggggggtg gggtggggca ggacagcaag ggggaggatt gggaagacaa   16260
```

```
tagcaggcat gctggggatg cggtgggctc tatggcttct gaggcggaaa gaacttaatt    16320
aactagctag aagatccggc tgctaacaaa gcccgaaagg aagctgagtt ggctgctgcc    16380
accgctgagc aataactagc ataacccctt ggggcctcta aacgggtctt gagggggtttt   16440 ttgctgaaag gaggaactat atccggatat cccgggagct tgtatatcca ttttcggatc    16500
tgatcaagag acaggatgag gatcgtttcg catgattgaa caagatggat tgcacgcagg    16560
ttctccggcc gcttgggtgg agaggctatt cggctatgac tgggcacaac agacaatcgg    16620
ctgctctgat gccgccgtgt tccggctgtc agcgcagggg cgcccggttc tttttgtcaa    16680
gaccgacctg tccggtgccc tgaatgaact gcaggacgag gcagcgcggc tatcgtggct    16740
ggccacgacg ggcgttcctt gcgcagctgt gctcgacgtt gtcactgaag cgggaaggga    16800
ctggctgcta ttgggcgaag tgccggggca ggatcctg tcatctcacc ttgctcctgc     16860
cgagaaagta tccatcatgg ctgatgcaat gcggcggctg catacgcttg atccggctac    16920
ctgcccattc gaccaccaag cgaaacatcg catcgagcga gcgtactc ggatggaagc      16980 cggtcttgtc gatcaggatg atctggacga agagcatcag gggctcgcgc cagccgaact    17040
gttcgccagg ctcaaggcgc gcatgcccga cggcgaggat ctcgtcgtga cccatggcga    17100
tgcctgcttg ccgaatatca tggtggaaaa tggccgcttt tctggattca tcgactgtgg    17160
ccggctgggt gtggcggacc gctatcagga catagcgttg gctacccgtg atattgctga    17220
agagcttggc ggcgaatggg ctgaccgctt cctcgtgctt tacggtatcg ccgctcccga    17280
ttcgcagcgc atcgccttct atcgccttct tgacgagttc ttctgagcgg gactctgggg    17340
ttcgaaatga ccgaccaagc gacgcccaac ctgccatcac gagatttcga ttccaccgcc    17400
gccttctatg aaaggttggg cttcggaatc gttttccggg acgccggctg gatgatcctc    17460
cagcgcgggg atctcatgct ggagttcttc gcccacccca acttgtttat tgcagcttat    17520
aatggttaca ataaagcaa tagcatcaca aatttcacaa ataaagcatt ttttcactg     17580 cattctagtt gtggtttgtc caaactcatc aatgtatctt atcatgtctg tataccgtcg    17640
acctctagct agagcttggc gtaatcatgg tcatagctgt ttcctgtgtg aaattgttat    17700
ccgctcacaa ttccacacaa catacgagcc ggaagcataa agtgtaaagc ctggggtgcc    17760
taatgagtga gctaactcac attaattgcg ttgcgctcac tgcccgcttt ccagtcggga    17820
aacctgtcgt gccagctgca ttaatgaatc ggccaacgcg cggggagagg cggtttgcgt    17880
attgggcgct cttccgcttc ctcgctcact gactcgctgc gctcggtcgt tcggctgcgg    17940
cgagcggtat cagctcactc aaaggcggta atacggttat ccacagaatc aggggataac    18000
gcaggaaaga acatgtgagc aaaaggccag caaaaggcca ggaaccgtaa aaaggccgcg    18060
ttgctggcgt ttttccatag gctccgcccc cctgacgagc atcacaaaaa tcgacgctca    18120
agtcagaggt ggcgaaaccc gacaggacta taaagatacc aggcgtttcc ccctggaagc    18180
tccctcgtgc gctctcctgt tccgaccctg ccgcttaccg gatacctgtc cgcctttctc    18240
ccttcgggaa gcgtggcgct ttctcatagc tcacgctgta ggtatctcag ttcggtgtag    18300
gtcgttcgct ccaagctggg ctgtgtgcac gaaccccccg ttcagcccga ccgctgcgcc    18360
ttatccggta actatcgtct tgagtccaac ccggtaagac acgacttatc gccactggca    18420
gcagccactg gtaacaggat tagcagagcg aggtatgtag gcggtgctac agagttcttg    18480
aagtggtggc ctaactacgg ctacactaga agaacagtat ttggtatctg cgctctgctg    18540
aagccagtta ccttcggaaa aagagttggt agctcttgat ccggcaaaca aaccaccgct    18600
```

```
ggtagcggtt tttttgtttg caagcagcag attacgcgca gaaaaaaagg atctcaagaa    18660
gatcctttga tcttttctac ggggtctgac gctcagtgga acgaaaactc acgttaaggg    18720
attttggtca tgagattatc aaaaaggatc ttcacctaga tccttttaaa ttaaaaatga    18780
agttttaaat caatctaaag tatatatgag taaacttggt ctgacagtta ccaatgctta    18840
atcagtgagg cacctatctc agcgatctgt ctatttcgtt catccatagt tgcctgactc    18900
cccgtcgtgt agataactac gatacgggag ggcttaccat ctggccccag tgctgcaatg    18960
ataccgcgag acccacgctc accggctcca gatttatcag caataaacca gccagccgga    19020
agggccgagc gcagaagtgg tcctgcaact ttatccgcct ccatccagtc tattaattgt    19080
tgccgggaag ctagagtaag tagttcgcca gttaatagtt tgcgcaacgt tgttgccatt    19140
gctacaggca tcgtggtgtc acgctcgtcg tttggtatgg cttcattcag ctccggttcc    19200
caacgatcaa ggcgagttac atgatccccc atgttgtgca aaaaagcggt tagctccttc    19260
ggtcctccga tcgttgtcag aagtaagttg gccgcagtgt tatcactcat ggttatggca    19320
gcactgcata attctcttac tgtcatgcca tccgtaagat gcttttctgt gactggtgag    19380
tactcaacca agtcattctg agaatagtgt atgcggcgac cgagttgctc ttgcccggcg    19440
tcaatacggg ataataccgc gccacatagc agaactttaa aagtgctcat cattggaaaa    19500
cgttcttcgg ggcgaaaact ctcaaggatc ttaccgctgt tgagatccag ttcgatgtaa    19560
cccactcgtg cacccaactg atcttcagca tcttttactt tcaccagcgt ttctgggtga    19620
gcaaaaacag gaaggcaaaa tgccgcaaaa aagggaataa gggcgacacg gaaatgttga    19680
atactcatac tcttcctttt tcaatattat tgaagcattt atcagggtta ttgtctcatg    19740
agcggataca tatttgaatg tatttagaaa aataaacaaa tagggtgttcc gcgcacattt    19800
ccccgaaaag tgccacctga cgtc                                            19824

<210> SEQ ID NO 2
<211> LENGTH: 2655
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (668)...(1396)

<400> SEQUENCE: 2
acgcgttcga gctcgccccg ttacataact tacggtaaat ggcccgcctg gctgaccgcc     60
caacgacccc cgcccattga cgtcaataat gacgtatgtt cccatagtaa cgccaatagg    120
gactttccat tgacgtcaat gggtggagta tttacggtaa actgcccact tggcagtaca    180
tcaagtgtat catatgccaa gtacgccccc tattgacgtc aatgacggta aatggcccgc    240
ctggcattat gcccagtaca tgaccttatg ggactttcct acttggcagt acatctacgt    300
attagtcatc gctattacca tggtgatgcg gttttggcag tacatcaatg ggcgtggata    360
gcggtttgac tcacggggat ttccaagtct ccaccccatt gacgtcaatg ggagtttgtt    420
ttggcaccaa aatcaacggg actttccaaa atgtcgtaac aactccgccc cattgacgca    480
aatgggcggt aggcgtgtac ggtgggaggt ctatataagc agagctcgtt tagtgaaccg    540
tcagatcgcc tggagacgcc atccacgctg ttttgacctc catagaagac accgggaccg    600
atccagcctc cggggatct tggtggcgtg aaactcccgc acctcttcgg ccagcgaatt    660 cgcgcgt atg ggg agt agc aag agc aag cct aag gac ccc agc cag cgc    709
         Met Gly Ser Ser Lys Ser Lys Pro Lys Asp Pro Ser Gln Arg
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 1   |     |     |     | 5   |     |     |     |     | 10  |     |     |     |     |     |      |
| tct | aga | ggc | gtc | caa | gtc | gaa | acc | att | agt | ccc | gga | gat | ggc | aga | aca | 757  |
| Ser | Arg | Gly | Val | Gln | Val | Glu | Thr | Ile | Ser | Pro | Gly | Asp | Gly | Arg | Thr |      |
| 15  |     |     |     |     | 20  |     |     |     |     | 25  |     |     |     |     | 30  |      |
| ttt | cct | aaa | agg | gga | caa | aca | tgt | gtc | gtc | cat | tat | aca | ggc | atg | ttg | 805  |
| Phe | Pro | Lys | Arg | Gly | Gln | Thr | Cys | Val | Val | His | Tyr | Thr | Gly | Met | Leu |      |
|     |     |     |     | 35  |     |     |     |     | 40  |     |     |     |     | 45  |     |      |
| gag | gac | ggc | aaa | aag | gtg | gac | agt | agt | aga | gat | cgc | aat | aaa | cct | ttc | 853  |
| Glu | Asp | Gly | Lys | Lys | Val | Asp | Ser | Ser | Arg | Asp | Arg | Asn | Lys | Pro | Phe |      |
|     |     |     | 50  |     |     |     |     | 55  |     |     |     |     | 60  |     |     |      |
| aaa | ttc | atg | ttg | gga | aaa | caa | gaa | gtc | att | agg | gga | tgg | gag | gag | ggc | 901  |
| Lys | Phe | Met | Leu | Gly | Lys | Gln | Glu | Val | Ile | Arg | Gly | Trp | Glu | Glu | Gly |      |
|     |     | 65  |     |     |     |     | 70  |     |     |     |     | 75  |     |     |     |      |
| gtg | gct | caa | atg | tcc | gtc | ggc | caa | cgc | gct | aag | ctc | acc | atc | agc | ccc | 949  |
| Val | Ala | Gln | Met | Ser | Val | Gly | Gln | Arg | Ala | Lys | Leu | Thr | Ile | Ser | Pro |      |
|     | 80  |     |     |     |     | 85  |     |     |     |     | 90  |     |     |     |     |      |
| gac | tac | gca | tac | ggc | gct | acc | gga | cat | ccc | gga | att | att | ccc | cct | cac | 997  |
| Asp | Tyr | Ala | Tyr | Gly | Ala | Thr | Gly | His | Pro | Gly | Ile | Ile | Pro | Pro | His |      |
| 95  |     |     |     | 100 |     |     |     |     | 105 |     |     |     |     | 110 |     |      |
| gct | acc | ttg | gtg | ttt | gac | gtc | gaa | ctg | ttg | aag | ctc | gag | act | aga | gga | 1045 |
| Ala | Thr | Leu | Val | Phe | Asp | Val | Glu | Leu | Leu | Lys | Leu | Glu | Thr | Arg | Gly |      |
|     |     |     |     | 115 |     |     |     |     | 120 |     |     |     |     | 125 |     |      |
| gtg | cag | gtg | gag | act | atc | tcc | cca | gga | gac | ggg | cgc | acc | ttc | ccc | aag | 1093 |
| Val | Gln | Val | Glu | Thr | Ile | Ser | Pro | Gly | Asp | Gly | Arg | Thr | Phe | Pro | Lys |      |
|     |     |     | 130 |     |     |     |     | 135 |     |     |     |     | 140 |     |     |      |
| cgc | ggc | cag | acc | tgc | gtg | gtg | cac | tac | acc | ggg | atg | ctt | gaa | gat | gga | 1141 |
| Arg | Gly | Gln | Thr | Cys | Val | Val | His | Tyr | Thr | Gly | Met | Leu | Glu | Asp | Gly |      |
|     |     | 145 |     |     |     |     | 150 |     |     |     |     | 155 |     |     |     |      |
| aag | aaa | gtt | gat | tcc | tcc | cgg | gac | aga | aac | aag | ccc | ttt | aag | ttt | atg | 1189 |
| Lys | Lys | Val | Asp | Ser | Ser | Arg | Asp | Arg | Asn | Lys | Pro | Phe | Lys | Phe | Met |      |
|     | 160 |     |     |     |     | 165 |     |     |     |     | 170 |     |     |     |     |      |
| cta | ggc | aag | cag | gag | gtg | atc | cga | ggc | tgg | gaa | gaa | ggg | gtt | gcc | cag | 1237 |
| Leu | Gly | Lys | Gln | Glu | Val | Ile | Arg | Gly | Trp | Glu | Glu | Gly | Val | Ala | Gln |      |
| 175 |     |     |     |     | 180 |     |     |     |     | 185 |     |     |     |     | 190 |      |
| atg | agt | gtg | ggt | cag | aga | gcc | aaa | ctg | act | ata | tct | cca | gat | tat | gcc | 1285 |
| Met | Ser | Val | Gly | Gln | Arg | Ala | Lys | Leu | Thr | Ile | Ser | Pro | Asp | Tyr | Ala |      |
|     |     |     | 195 |     |     |     |     | 200 |     |     |     |     | 205 |     |     |      |
| tat | ggt | gcc | act | ggg | cac | cca | ggc | atc | atc | cca | cca | cat | gcc | act | ctc | 1333 |
| Tyr | Gly | Ala | Thr | Gly | His | Pro | Gly | Ile | Ile | Pro | Pro | His | Ala | Thr | Leu |      |
|     |     | 210 |     |     |     |     | 215 |     |     |     |     | 220 |     |     |     |      |
| gtc | ttc | gat | gtg | gag | ctt | cta | aaa | ctg | gaa | act | agt | tat | ccg | tac | gac | 1381 |
| Val | Phe | Asp | Val | Glu | Leu | Leu | Lys | Leu | Glu | Thr | Ser | Tyr | Pro | Tyr | Asp |      |
|     | 225 |     |     |     |     | 230 |     |     |     |     | 235 |     |     |     |     |      |
| gta | cca | gac | tac | gca | taagaaagt | | | gaggatcctg | | | agaacttcag | | | ggtgagtttg | | | 1436 |
| Val | Pro | Asp | Tyr | Ala | | | | | | | | | | | | |
|     | 240 |     |     |     | | | | | | | | | | | | |

| | |
|---|---|
| gggacccttg attgttcttt cttttcgct attgtaaaat tcatgttata tggaggggc | 1496 |
| aaagttttca gggtgttgtt tagaatggga agatgtccct tgtatcacca tggaccctca | 1556 |
| tgataatttt gtttctttca ctttctactc tgttgacaac cattgtctcc tcttattttc | 1616 |
| ttttcatttt ctgtaacttt ttcgttaaac tttagcttgc atttgtaacg aattttaaa | 1676 |
| ttcacttttg tttatttgtc agattgtaag tactttctct aatcacttttt ttttcaaggc | 1736 |
| aatcagggta tattatattg tacttcagca cagttttaga gaacaattgt tataattaaa | 1796 |
| tgataaggta gaatatttct gcatataaat tctggctggc gtggaaatat tcttattggt | 1856 |
| agaaacaact acatcctggt catcatcctg cctttctctt tatggttaca atgatataca | 1916 |
| ctgtttgaga tgaggataaa atactctgag tccaaaccgg gcccctctgc taaccatgtt | 1976 |

-continued

```
catgccttct tcttttcct acagctcctg ggcaacgtgc tggttgttgt gctgtctcat    2036
cattttggca aaggattcac tcctcaggtg caggctgcct atcagaaggt ggtggctggt    2096
gtggccaatg ccctggctca caaataccac tgagatcttt tccctctgc caaaaattat    2156 ggggacatca tgaagcccct tgagcatctg acttctggct aataaaggaa atttattttc    2216
attgcaatag tgtgttggaa ttttttgtgt ctctcactcg aaggacata tgggagggca    2276 aatcatttaa aacatcagaa tgagtatttg gtttagagtt tggcaacata tgccatatgc    2336
tggctgccat gaacaaaggt ggctataaag aggtcatcag tatatgaaac agcccctgc     2396 tgtccattcc ttattccata gaaaagcctt gacttgaggt tagatttttt ttatattttg    2456
ttttgtgtta tttttttctt taacatccct aaaattttcc ttacatgttt tactagccag    2516
atttttcctc ctctcctgac tactcccagt catagctgtc cctcttctct tatgaagatc    2576
cctcgaggag cttttgcaa agccctagg cctccaaaaa agcctcttca ctacttctgg      2636
aatagctcag aggccgagg                                                 2655
```

<210> SEQ ID NO 3
<211> LENGTH: 108
<212> TYPE: PRT
<213> ORGANISM: Bos taurus

<400> SEQUENCE: 3

Met Gly Val Gln Val Lys Thr Ile Ser Pro Gly Asp Gly Arg Thr Phe
  1               5                  10                  15

Pro Lys Arg Gly Gln Thr Cys Val Val His Tyr Thr Gly Met Leu Glu
             20                  25                  30

Asp Gly Lys Lys Phe Asp Ser Ser Arg Asp Arg Asn Lys Pro Phe Lys
         35                  40                  45

Phe Val Leu Gly Lys Gln Glu Val Ile Arg Gly Trp Glu Glu Trp Val
     50                  55                  60

Ala Gln Met Ser Val Gly Gln Arg Ala Lys Leu Thr Ile Ser Pro Asp
 65                  70                  75                  80

Tyr Ala Tyr Gly Ala Thr Gly His Pro Gly Ile Ile Pro Pro Asn Ala
                 85                  90                  95

Thr Leu Ile Phe Asp Val Glu Phe Leu Lys Leu Glu
            100                 105

<210> SEQ ID NO 4
<211> LENGTH: 108
<212> TYPE: PRT
<213> ORGANISM: Bos taurus

<400> SEQUENCE: 4

Met Gly Val Glu Ile Glu Thr Ile Ser Pro Gly Asp Gly Arg Thr Phe
  1               5                  10                  15

Pro Lys Lys Gly Gln Thr Cys Val Val His Tyr Thr Gly Met Leu Gln
             20                  25                  30

Asn Gly Lys Lys Phe Asp Ser Ser Arg Asp Arg Asn Lys Pro Phe Lys
         35                  40                  45

Phe Arg Ile Gly Lys Gln Glu Val Ile Lys Gly Phe Glu Glu Gly Ala
     50                  55                  60

Ala Gln Met Ser Leu Gly Gln Arg Ala Lys Leu Thr Cys Thr Pro Asp
 65                  70                  75                  80

Val Ala Tyr Gly Ala Thr Gly His Pro Gly Val Ile Pro Pro Asn Ala
                 85                  90                  95

```
Thr Leu Ile Phe Asp Val Glu Leu Leu Asn Leu Glu
            100                 105
```

<210> SEQ ID NO 5
<211> LENGTH: 108
<212> TYPE: PRT
<213> ORGANISM: Rattus norvegicus

<400> SEQUENCE: 5

```
Met Gly Val Gln Val Glu Thr Ile Ser Ser Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Thr Leu Gly Lys Gln Glu Val Ile Arg Gly Trp Glu Glu Gly Val
    50                  55                  60

Ala Gln Met Ser Val Gly Gln Arg Ala Lys Leu Ile Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105
```

<210> SEQ ID NO 6
<211> LENGTH: 108
<212> TYPE: PRT
<213> ORGANISM: Rattus norvegicus

<400> SEQUENCE: 6

```
Met Gly Val Glu Ile Glu Thr Ile Ser Pro Gly Asp Gly Arg Thr Phe
1               5                   10                  15

Pro Lys Lys Gly Gln Ile Cys Val Val His Tyr Thr Gly Met Leu Gln
            20                  25                  30

Asn Gly Lys Lys Phe Asp Ser Ser Arg Asp Arg Asn Lys Pro Phe Lys
        35                  40                  45

Phe Arg Ile Gly Lys Gln Glu Val Ile Lys Gly Phe Glu Glu Gly Ala
    50                  55                  60

Ala Gln Met Ser Leu Gly Gln Arg Ala Lys Leu Thr Cys Thr Pro Asp
65                  70                  75                  80

Val Ala Tyr Gly Ala Thr Gly His Pro Gly Val Ile Pro Pro Asn Ala
                85                  90                  95

Thr Leu Ile Phe Asp Val Glu Leu Leu Asn Leu Glu
            100                 105
```

<210> SEQ ID NO 7
<211> LENGTH: 108
<212> TYPE: PRT
<213> ORGANISM: Mus musculus

<400> SEQUENCE: 7

```
Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45
```

```
Phe Thr Leu Gly Lys Gln Glu Val Ile Arg Gly Trp Glu Glu Gly Val
         50                  55                  60
Ala Gln Met Ser Val Gly Gln Arg Ala Lys Leu Ile Ile Ser Ser Asp
 65                  70                  75                  80
Tyr Ala Tyr Gly Ala Thr Gly His Pro Gly Ile Ile Pro Pro His Ala
                 85                  90                  95
Thr Leu Val Phe Asp Val Glu Leu Leu Lys Leu Glu
                100                 105
```

<210> SEQ ID NO 8
<211> LENGTH: 108
<212> TYPE: PRT
<213> ORGANISM: Mus musculus

<400> SEQUENCE: 8

```
Met Gly Val Glu Ile Glu Thr Ile Ser Pro Gly Asp Gly Arg Thr Phe
 1               5                  10                  15
Pro Lys Lys Gly Gln Ile Cys Val Val His Tyr Thr Gly Met Leu Gln
                 20                  25                  30
Lys Gly Lys Lys Phe Asp Ser Ser Arg Asp Arg Asn Lys Pro Phe Lys
             35                  40                  45
Phe Arg Ile Gly Lys Gln Glu Val Ile Lys Gly Phe Glu Glu Gly Thr
         50                  55                  60
Ala Gln Met Ser Leu Gly Gln Arg Ala Lys Leu Thr Cys Thr Pro Asp
 65                  70                  75                  80
Val Ala Tyr Gly Ala Thr Gly His Pro Gly Val Ile Pro Pro Asn Ala
                 85                  90                  95
Thr Leu Ile Phe Asp Val Glu Leu Leu Ser Leu Glu
                100                 105
```

<210> SEQ ID NO 9
<211> LENGTH: 108
<212> TYPE: PRT
<213> ORGANISM: Macaca mulata

<400> SEQUENCE: 9

```
Met Gly Val Gln Val Glu Thr Ile Ser Pro Gly Asp Gly Arg Thr Phe
 1               5                  10                  15
Pro Lys Arg Gly Gln Thr Cys Val Val His Tyr Thr Gly Met Leu Glu
                 20                  25                  30
Asp Gly Lys Lys Phe Asp Ser Ser Arg Asp Arg Asn Lys Pro Phe Lys
             35                  40                  45
Phe Met Leu Gly Lys Gln Glu Val Ile Arg Gly Trp Glu Glu Gly Val
         50                  55                  60
Ala Gln Met Ser Val Gly Gln Arg Ala Lys Leu Thr Ile Ser Pro Asp
 65                  70                  75                  80
Tyr Ala Tyr Gly Ala Thr Gly His Pro Gly Ile Ile Pro Pro His Ala
                 85                  90                  95
Thr Leu Val Phe Asp Val Glu Leu Leu Lys Leu Glu
                100                 105
```

<210> SEQ ID NO 10
<211> LENGTH: 108
<212> TYPE: PRT
<213> ORGANISM: Macaca mulata

<400> SEQUENCE: 10

```
Met Gly Val Glu Ile Glu Thr Ile Ser Pro Gly Asp Gly Arg Thr Phe
```

```
                1               5                  10                  15
        Pro Lys Lys Gly Gln Thr Cys Val Val His Tyr Thr Gly Met Leu Gln
                        20                  25                  30

Asn Gly Lys Lys Phe Asp Ser Ser Arg Asp Arg Asn Lys Pro Phe Lys
                    35                  40                  45

Phe Arg Ile Gly Lys Gln Glu Val Ile Lys Gly Phe Glu Glu Gly Ala
                50                  55                  60

Ala Gln Met Ser Leu Gly Gln Arg Ala Lys Leu Thr Cys Thr Pro Asp
        65                  70                  75                  80

Val Ala Tyr Gly Ala Thr Gly His Pro Gly Val Ile Pro Pro Asn Ala
                        85                  90                  95

Thr Leu Ile Phe Asp Val Glu Leu Leu Asn Leu Glu
                    100                 105

<210> SEQ ID NO 11
<211> LENGTH: 108
<212> TYPE: PRT
<213> ORGANISM: Pan troglodytes

<400> SEQUENCE: 11

Met Gly Val Gln Val Glu Thr Ile Ser Pro Gly Asp Gly Arg Thr Phe
        1               5                   10                  15

Pro Lys Arg Gly Gln Thr Cys Val Val His Tyr Thr Gly Met Leu Glu
                        20                  25                  30

Asp Gly Lys Lys Phe Asp Ser Ser Arg Asp Arg Asn Lys Pro Phe Lys
                    35                  40                  45

Phe Met Leu Gly Lys Gln Glu Val Ile Arg Gly Trp Glu Glu Gly Val
                50                  55                  60

Ala Gln Met Ser Val Gly Gln Arg Ala Lys Leu Thr Ile Ser Pro Asp
        65                  70                  75                  80

Tyr Ala Tyr Gly Ala Thr Gly His Pro Gly Ile Ile Pro Pro His Ala
                        85                  90                  95

Thr Leu Val Phe Asp Val Glu Leu Leu Lys Leu Glu
                    100                 105

<210> SEQ ID NO 12
<211> LENGTH: 108
<212> TYPE: PRT
<213> ORGANISM: Pan troglodytes

<400> SEQUENCE: 12

Met Gly Val Glu Ile Glu Thr Ile Ser Pro Gly Asp Gly Arg Thr Phe
        1               5                   10                  15

Pro Lys Lys Gly Gln Thr Cys Val Val His Tyr Thr Gly Met Leu Gln
                        20                  25                  30

Asn Gly Lys Lys Phe Asp Ser Ser Arg Asp Arg Asn Lys Pro Phe Lys
                    35                  40                  45

Phe Arg Ile Gly Lys Gln Glu Val Ile Lys Gly Phe Glu Glu Gly Ala
                50                  55                  60

Ala Gln Met Ser Leu Gly Gln Arg Ala Lys Leu Thr Cys Thr Pro Asp
        65                  70                  75                  80

Val Ala Tyr Gly Ala Thr Gly His Pro Gly Val Ile Pro Pro Asn Ala
                        85                  90                  95

Thr Leu Ile Phe Asp Val Glu Leu Leu Asn Leu Glu
                    100                 105
```

-continued

```
<210> SEQ ID NO 13
<211> LENGTH: 108
<212> TYPE: PRT
<213> ORGANISM: Homo sapiens

<400> SEQUENCE: 13

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 14
<211> LENGTH: 108
<212> TYPE: PRT
<213> ORGANISM: Homo sapiens

<400> SEQUENCE: 14

Met Gly Val Glu Ile Glu Thr Ile Ser Pro Gly Asp Gly Arg Thr Phe
1               5                   10                  15

Pro Lys Lys Gly Gln Thr Cys Val Val His Tyr Thr Gly Met Leu Gln
            20                  25                  30

Asn Gly Lys Lys Phe Asp Ser Ser Arg Asp Arg Asn Lys Pro Phe Lys
        35                  40                  45

Phe Arg Ile Gly Lys Gln Glu Val Ile Lys Gly Phe Glu Glu Gly Ala
    50                  55                  60

Ala Gln Met Ser Leu Gly Gln Arg Ala Lys Leu Thr Cys Thr Pro Asp
65                  70                  75                  80

Val Ala Tyr Gly Ala Thr Gly His Pro Gly Val Ile Pro Pro Asn Ala
                85                  90                  95

Thr Leu Ile Phe Asp Val Glu Leu Leu Asn Leu Glu
            100                 105

<210> SEQ ID NO 15
<211> LENGTH: 107
<212> TYPE: PRT
<213> ORGANISM: Artificial Sequence
<220> FEATURE:
<223> OTHER INFORMATION: Synthetically generated peptide

<400> SEQUENCE: 15

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60
```

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 16
<211> LENGTH: 109
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 4
<223> OTHER INFORMATION: Xaa = Glu or Gln
<220> FEATURE:
<221> NAME/KEY: VARIANT
<222> LOCATION: 5
<223> OTHER INFORMATION: Xaa = Ile or Val
<220> FEATURE:
<221> NAME/KEY: VARIANT
<222> LOCATION: 6
<223> OTHER INFORMATION: Xaa = Glu or Lys
<220> FEATURE:
<221> NAME/KEY: VARIANT
<222> LOCATION: 32
<223> OTHER INFORMATION: Xaa = Gln or Glu
<220> FEATURE:
<221> NAME/KEY: VARIANT
<222> LOCATION: 33
<223> OTHER INFORMATION: Xaa = Asn, Asp or Lys
<220> FEATURE:
<221> NAME/KEY: VARIANT
<222> LOCATION: 37...
<223> OTHER INFORMATION: Xaa = Phe or Val
<220> FEATURE:
<221> NAME/KEY: VARIANT
<222> LOCATION: 50
<223> OTHER INFORMATION: Xaa = Arg or Met
<220> FEATURE:
<221> NAME/KEY: VARIANT
<222> LOCATION: 51
<223> OTHER INFORMATION: Xaa = Ile or Leu
<220> FEATURE:
<221> NAME/KEY: VARIANT
<222> LOCATION: 58
<223> OTHER INFORMATION: Xaa = Lys or Arg
<220> FEATURE:
<221> NAME/KEY: VARIANT
<222> LOCATION: 60
<223> OTHER INFORMATION: Xaa = Phe or Trp
<220> FEATURE:
<221> NAME/KEY: VARIANT
<222> LOCATION: 63
<223> OTHER INFORMATION: Xaa = Glu or Trp
<220> FEATURE:
<221> NAME/KEY: VARIANT
<222> LOCATION: 64
<223> OTHER INFORMATION: Xaa = Gly or Val
<220> FEATURE:
<221> NAME/KEY: VARIANT
<222> LOCATION: 69)
<223> OTHER INFORMATION: Xaa = Ser or Val
<220> FEATURE:
<221> NAME/KEY: VARIANT
<222> LOCATION: 76
<223> OTHER INFORMATION: Xaa = Leu or Ile
<220> FEATURE:
<221> NAME/KEY: VARIANT
<222> LOCATION: 77
<223> OTHER INFORMATION: Xaa = Thr or Ile
<220> FEATURE:
<221> NAME/KEY: VARIANT
<222> LOCATION: 78

```
<223> OTHER INFORMATION: Xaa = Cys or Ser
<220> FEATURE:
<221> NAME/KEY: VARIANT
<222> LOCATION: 81
<223> OTHER INFORMATION: Xaa = Asp or Tyr
<220> FEATURE:
<221> NAME/KEY: VARIANT
<222> LOCATION: 91
<223> OTHER INFORMATION: Xaa = Gly or Ile
<220> FEATURE:
<221> NAME/KEY: VARIANT
<222> LOCATION: 96
<223> OTHER INFORMATION: Xaa = Asn or His
<220> FEATURE:
<221> NAME/KEY: VARIANT
<222> LOCATION: 99
<223> OTHER INFORMATION: Xaa = Leu or Val
<220> FEATURE:
<221> NAME/KEY: VARIANT
<222> LOCATION: 104
<223> OTHER INFORMATION: Xaa = Glu or Phe
<220> FEATURE:
<221> NAME/KEY: VARIANT
<222> LOCATION: 106
<223> OTHER INFORMATION: Xaa = Leu or Lys

<400> SEQUENCE: 16

Met Gly Val Xaa Xaa Thr Ile Ser Pro Gly Asp Gly Arg Thr Phe
 1               5                  10                  15

Pro Lys Lys Gly Gln Thr Cys Val Val His Tyr Thr Gly Met Leu Xaa
                20                  25                  30

Xaa Gly Lys Lys Xaa Asp Ser Ser Arg Asp Arg Asn Lys Pro Phe Lys
            35                  40                  45

Phe Xaa Xaa Gly Lys Gln Glu Val Ile Xaa Gly Xaa Phe Glu Xaa Xaa
50                  55                  60

Ala Ala Gln Met Xaa Leu Gly Gln Arg Ala Lys Xaa Xaa Xaa Thr Pro
65                  70                  75                  80

Xaa Val Ala Tyr Gly Ala Thr Gly His Pro Xaa Val Ile Pro Pro Xaa
                85                  90                  95

Ala Thr Xaa Ile Phe Asp Val Xaa Leu Xaa Asn Leu Glu
            100                 105

<210> SEQ ID NO 17
<211> LENGTH: 243
<212> TYPE: PRT
<213> ORGANISM: Artificial Sequence
<220> FEATURE:
<223> OTHER INFORMATION: Synthetically generated peptide

<400> SEQUENCE: 17

Met Gly Ser Ser Lys Ser Lys Pro Lys Asp Pro Ser Gln Arg Ser Arg
 1               5                  10                  15

Gly Val Gln Val Glu Thr Ile Ser Pro Gly Asp Gly Arg Thr Phe Pro
                20                  25                  30

Lys Arg Gly Gln Thr Cys Val Val His Tyr Thr Gly Met Leu Glu Asp
            35                  40                  45

Gly Lys Lys Val Asp Ser Ser Arg Asp Arg Asn Lys Pro Phe Lys Phe
50                  55                  60

Met Leu Gly Lys Gln Glu Val Ile Arg Gly Trp Glu Glu Gly Val Ala
65                  70                  75                  80

Gln Met Ser Val Gly Gln Arg Ala Lys Leu Thr Ile Ser Pro Asp Tyr
                85                  90                  95

Ala Tyr Gly Ala Thr Gly His Pro Gly Ile Ile Pro Pro His Ala Thr
                100                 105                 110
```

```
Leu Val Phe Asp Val Glu Leu Leu Lys Leu Glu Thr Arg Gly Val Gln
            115                 120                 125

Val Glu Thr Ile Ser Pro Gly Asp Gly Arg Thr Phe Pro Lys Arg Gly
        130                 135                 140

Gln Thr Cys Val Val His Tyr Thr Gly Met Leu Glu Asp Gly Lys Lys
145                 150                 155                 160

Val Asp Ser Ser Arg Asp Arg Asn Lys Pro Phe Lys Phe Met Leu Gly
                165                 170                 175

Lys Gln Glu Val Ile Arg Gly Trp Glu Glu Gly Val Ala Gln Met Ser
                180                 185                 190

Val Gly Gln Arg Ala Lys Leu Thr Ile Ser Pro Asp Tyr Ala Tyr Gly
            195                 200                 205

Ala Thr Gly His Pro Gly Ile Ile Pro Pro His Ala Thr Leu Val Phe
        210                 215                 220

Asp Val Glu Leu Leu Lys Leu Glu Thr Ser Tyr Pro Tyr Asp Val Pro
225                 230                 235                 240

Asp Tyr Ala

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ccaccatggg gagtagcaag ag                                          22

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
ggaattctta gtcgagtgcg tagt                                        24
```

CONDITIONAL-STOP DIMERIZABLE CASPASE TRANSGENIC ANIMALS

CLAIM OF PRIORITY

This application claims the benefit of U.S. Patent Application Ser. No. 61/020,666, filed on Jan. 11, 2008, the entire contents of which are hereby incorporated by reference.

TECHNICAL FIELD

This invention relates to transgenic animals, e.g., transgenic mice, with a time- and tissue-controllable death gene, constructs and cells useful in the creation of said animals, and cells derived from said animals.

BACKGROUND

A number of degenerative human diseases are characterized by the loss of specific cells in adult tissues. The availability and creation of animal models for these diseases has been hampered by the lack of a system to create models in which apoptosis can be induced in a time- and tissue-specific manner.

SUMMARY

Described herein is a transgenic mouse with an inducible caspase gene for targeted cell ablation. The transgene construct contains a bioengineered dimerizable caspase-3 gene under a stop-flox sequence, in some embodiments, the gene results in mosaic patterned, binary expression of product after recombination. Tissue specificity is determined by the choice of a Cre mouse: intersection of transgene driven by a promoter and Cre-recombinase under a promoter of choice drives engineered caspase monomer expression. The timing of cell death is controlled by administration of a dimerizer which specifically binds to a dimerizing sequence, e.g., the Fv sequence (e.g., from Ariad Inc), located upstream of caspase-3. Because caspase-3 is rapidly activated after it is dimerized, targeted cells are rapidly ablated through apoptosis after exposure to the dimerizer.

A major advantage of this mouse is the ability to achieve tissue specificity by crossing with any Cre-expressing mouse, and the inducing cell killing in the adult by administration of the chemical inducer of dimerization. The timing of Cre expression is therefore not critical and whenever the Cre transgene is expressed the cell type marked by that gene will begin expressing caspase. Therefore, cell death can be controlled by the timing of administration of the dimerizer. This approach differs from previous approaches in which a single promoter was placed upstream of the caspase sequence because a mouse that contains the floxed STOP sequence can be used to create models for numerous cell types by crossing this new mouse with Cre mice that cover the expression of many genes. The approach also differs from the Cre-Lox approach in which a death gene is expressed as soon as a STOP sequence is removed, because in the present mice the caspase gene is inducible and is only activated after administration of the chemical inducer of dimerization to the animals that have activated the gene in the floxed cells. This allows access to a far larger pool of tissues that can be specifically ablated, including tissues that display specific Cre expression only for example during embryogenesis. This is significant when considering a tissue for targeting since many tissue specific markers are only expressed during development.

The transgenic animals described herein, e.g., mice, can be used for the targeted ablation of any cell type. These animals can be used, e.g., for the construction of models for diseases, e.g., diseases in which cells in a particular organ or tissue, or multiple organs or tissues, die. The animals can also be used as cancer models, in which a tumor formed in the animal's tissue can subsequently be destroyed by induction of caspase in that tissue. The animals can also be used to make models of cell loss and tissue degeneration, e.g., for the purpose of testing strategies for replacing the lost cells. In addition, these mice can be used experimentally to understand physiological processes and pathways, e.g., to understand the role of a specific cell type in a neural pathway, such as a sound or visual input processing pathway.

As described herein, in some embodiments not all cells of the animal express the transgene, e.g., the animals are mosaics, and are thus useful models for the onset of degenerative diseases, e.g., when the process of cell loss is ongoing, or when cell loss is only partial. In some embodiments, the double transgenic animals are mosaics as a result of incomplete recombination and mosaic expression of the transgene.

Thus, in one aspect, the invention provides transgenic non-human mammals, e.g., mice, that have a recombinant nucleic acid molecule stably integrated into their genome. This nucleic acid molecule includes a sequence encoding a fusion protein; the fusion protein includes a cell-killing gene, e.g., a caspase, e.g., caspase 3, 8, or 9, linked in frame with a FK Binding Protein (FKBP) or variant thereof, wherein the caspase is downstream of a conditional-STOP cassette as described herein. In some embodiments, the nucleic acid molecule includes (i) a promoter;
(ii) downstream of said promoter, a conditional-STOP cassette including a coding region of a protein, e.g., a non-toxic protein, e.g., a reporter protein, and a stop-transcription sequence, e.g., a polyadenylation signal, flanked on either side by a recombinase recognition site; and
(iii) downstream of said conditional-STOP cassette, a sequence encoding a fusion protein including a cell killing gene, e.g., a caspase, e.g., caspase 3, 8, or 9, linked in frame with a FK Binding Protein (FKBP) or variant thereof, wherein said fusion protein is not expressed when said conditional-STOP cassette is present in the construct.

In some embodiments, expression of a recombinase in a cell of said mammal results in expression of said fusion protein, and exposure of said mammal to an FKBP dimerizing agent results in death of said cells expressing recombinase.

In some embodiments, said recombinant nucleic acid molecule is operably linked to one or more regulatory sequences, e.g., a promoter.

In another aspect, the invention provides cells isolated from the non-human animals, e.g., stem cells or germ cells.

Also provided herein are methods for the production of transgenic non-human mammals, e.g., rodents, e.g., mice. The methods include introducing a recombinant nucleic acid molecule into a germ cell, an embryonic cell, or an egg cell. In some embodiments, the recombinant nucleic acid molecule includes:

(i) a promoter;
(ii) downstream of said promoter, a conditional-STOP cassette including a coding region of a protein, e.g., a non-toxic protein, e.g., a reporter protein, and polyadenylation signal, flanked on either side by a recombinase recognition site; and
(iii) downstream of said conditional-STOP cassette, a sequence encoding a fusion protein comprising a cell-killing gene, e.g., a caspase, e.g., caspase 3, 8, or 9, linked in frame with a FK Binding Protein (FKBP) or variant thereof, wherein said fusion protein is not expressed when said conditional-STOP cassette is present in the construct.

In some embodiments, the methods further include crossing said transgenic non-human mammal with a second non-human mammal, wherein at least some of the cells of said second mammal express a recombinase that binds to and excises said stop sequence.

In another aspect, the invention provides a vector including:

(i) a promoter;

(ii) downstream of said promoter, a conditional-STOP cassette including a coding region of a non-toxic protein, e.g., a reporter protein, and polyadenylation signal, flanked on either side by a recombinase recognition site; and (iii) downstream of said conditional-STOP cassette, a sequence encoding a fusion protein including a cell-killing gene, e.g., a caspase, e.g., caspase 3, 8, or 9, linked in frame with a FK Binding Protein (FKBP) or variant thereof, wherein said fusion protein is not expressed when said conditional-STOP cassette is present in the construct.

In some embodiments, the vector also includes one or more selection markers, e.g., negative selection markers or antibiotic resistance genes, e.g., a neomycin resistance gene, e.g., PGK-Neo. In some embodiments, the vector is a viral vector, e.g., adenoviral, retroviral, or lentiviral vector.

In some embodiments, the recombinase recognition sequence is a lox sequence, e.g., selected from the group consisting of LoxP, Lox 66, Lox 71, Lox 511, Lox 512, and Lox 514, and variants thereof. In some embodiments, the recombinase recognition sequence is a FLT sequence.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Among the advantages of the present mice over other caspase models is the fact that other models were targeted at specific cell types, i.e., they were not general models that could be crossed to any Cre mouse to create new models of degeneration. In addition, an advantage over other models that use other toxic genes, including diphtheria toxin (Ivanova et al., Genesis 43:129-135 (2005)), is that these often also target single genes; in addition, unlike the present animals that use an inducible system, those models that use a Cre-Lox strategy to allow crossing to various Cre drivers generally do not allow for temporal control of the cell death.

Other features and advantages of the invention will be apparent from the following detailed description and figures, and from the claims.

DESCRIPTION OF DRAWINGS

FIG. 3 is the sequence of a portion of the pC4M-Fv2E vector, which is useful in creating the fusion proteins described herein, including two FKBP sequences, one of which is the 36V FKBP (Amara et al., Proc. Natl. Acad. Sci. U.S.A. 94:10618-23 (1997)), and the other of which has several silent mutations (SEQ ID NO:2), which significantly reduce the match between the FV domains at the nucleotide level, reducing potential for recombination.

FIG. 4 is sequence alignment of FKBP 1 from *Bos Taurus, Rattus norvegicus, Mus musculus, Macaca mulata, Pan troglodytes* and *Homo sapiens*. The sequence identifiers are shown in the right hand column of the figure. An asterisk in the consensus sequence (SEQ ID NO:16) indicates the presence of alternative residues, shown below the consensus sequence as alternatives 1, 2, and 3.

FIG. 5 is a schematic illustration of the one embodiment of the present invention, illustrating a plasmid and strategy for use thereof.

FIG. 6A is a bar graph showing viability by MTT assay of cells transfected with the dimerizable caspase, in the absence and presence of the dimerizing agent AP20187.

FIGS. 6B-6C are bar graphs showing cell viability (6B) and dead cells (6C) in the presence and absence of AP20187 and Cre.

FIG. 7 is a table showing the results of analysis of seven F1 animals.

FIGS. 8A-C are schematic illustrations showing the expression of lac Z (8A) or the transgene (8B-C) in cells where transgene is driven by CMV promoter in the absence (8A) or presence (8B-C) of Cre recombinase. FIG. 8B is the cell in the absence of the dimerizer; 8C shows the cell in the presence of the dimerizer.

FIGS. 9A-9F are bar graphs showing changes in auditory brain response (ABR) after dimerizer administration in Brn3c double Tg animals.

FIG. 11A is a bar graph showing effect of dimerizing agent on IGTT results in Ins-Cre double Tg animals.

FIGS. 11B-11C are bar graphs showing the effect of dimerizing agent on IGTT results in the same population of Ins-Cre double Tg animals shown in FIG. 11A, divided by sex (female, 11B; male, 11C).

DETAILED DESCRIPTION

Figure 1:
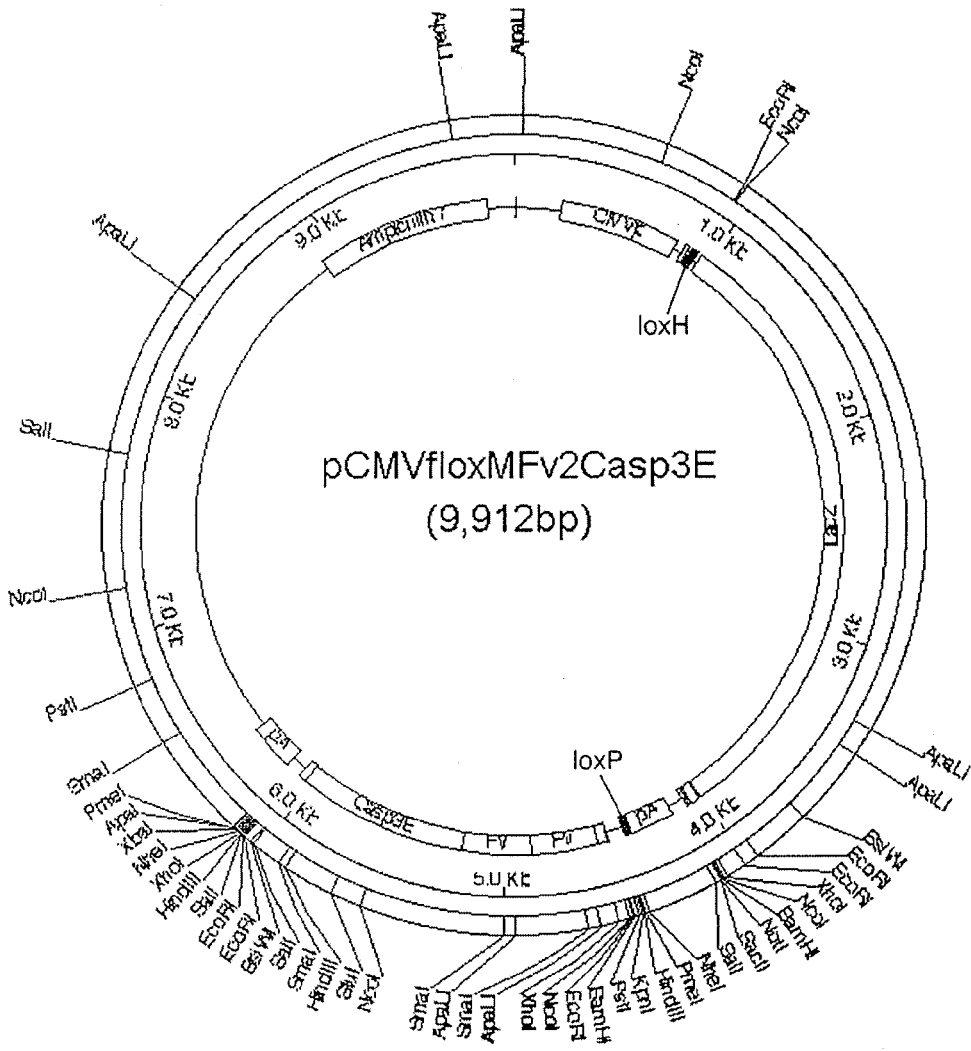
FIG. 1 is a schematic illustration of a plasmid containing a conditional stop caspase-3 and a CMV promoter.

Described herein are transgenic animal models for timed ablation of specific cell types. The timing of ablation is controlled by dimerization of Caspase-3 using a synthetic protein, and tissue/cell specific targeting is achieved using a recombinase under the control of a cell/tissue specific promoter. For example, described are transgenic mice that have an inducible apoptosis-inducing sequence, e.g., a sequence encoding a dimerizable caspase-3 downstream of a conditional-STOP cassette, which is a coding sequence (e.g., for a reporter such as lacZ, GFP, RFP, luciferase, or V5; a number of suitable reporters are known in the art) with a polyadenylation signal, flanked by a recombinase recognition sequence (e.g., a lox or lrt sequence), downstream of a promoter, e.g., a strong promoter such as CMV, β-actin, ROSA26, or any other ubiquitous or tissue-specific promoter. The conditional-STOP cassette prevents expression of the downstream dimerizable caspase sequence until a cell containing the conditional-STOP caspase sequence is exposed to Cre recombinase. The caspase is regulated by a sequence encoding a dimerizable protein, e.g., an FK506 binding protein (FKBP) or variant thereof, that is cloned in frame with the sequence encoding the caspase to form a fusion protein thereof, i.e., a dimerizable caspase. The caspase is thus made as a fusion protein in which the caspase is attached to an FKBP or variant that can be dimerized by addition of a dimerizing agent, e.g., FK506 or an analog thereof, that acts as an inducer of dimerization. The whole construct, including the conditional-STOP cassette plus the dimerizable caspase sequence and the promoter, is referred to herein as a "conditional-STOP dimerizable caspase" or simply "conditional-STOP caspase."

The conditional-STOP dimerizable caspase animals described herein can be crossed with animals (of the same species) expressing a recombinase, e.g., cyclization recombination (Cre) recombinase or flippase (Flp) recombinase, e.g., expressing the recombinase in a tissue- or cell-specific manner, or alternatively engineered to express the recombinase. Thus the recombinase can be ubiquitously expressed, or expressed in a tissue- or developmental stage-restricted manner, using methods known in the art.

When the conditional-STOP dimerizable caspase animals described herein are crossed with recombinase-expressing animals, the inducible caspase gene will be expressed only in those cells in which the recombinase is expressed. The activation of cell death takes place when the caspase was activated, and the caspase is activated only when a dimerizing agent (e.g., FK506 or an analog thereof) is administered to the animal. To direct the expression of the recombinase to a specific tissue, the recombinase can be expressed under the control of a promoter that is specific to a given tissue. A number of suitable recombinase-expressing animals are known in the art, and new ones can be created using methods known in the art.

In some embodiments, an inducible recombinase can be used. For example, a Cre recombinase can be expressed as a fusion protein with a mutant form of the mouse estrogen receptor ligand binding domain; administration of an estrogen analog (e.g., Tamoxifen) translocates the fusion protein to the nuclear compartment where it is active (see, e.g., Hayashi and McMahon, Dev Biol 244(2):305-18 (2002)). Such mice are commercially available, e.g., from Jackson Laboratory, Bar Harbor, Me. (e.g., the JAX® GEMM® Strain).

As one example, the conditional-STOP caspase mouse can be crossed with an Ins-Cre mouse (see, e.g., Ray et al., Int. J. Pancreatol. 25(3):157-63 (1999)), which expresses Cre under the control of the insulin promoter. In the offspring, the conditional-STOP caspase sequence will be expressed in the beta cells of the pancreas, where the insulin promoter drives the expression of Cre. Administration of the dimerizing agent (e.g., FK506 or an analog thereof) activates the dimerizable caspase in the beta cells of the pancreas. The dimerized caspase kills the cells, and the mouse then develops diabetes. In this way the timing of the inducible death can be determined, and both the time and location of cell death can be controlled.

Cre mice, e.g., mice that express Cre at a discrete time period during development (such as GATA3-Cre), can be crossed with the conditional-STOP caspase mice described herein, since the STOP sequence would be removed and the caspase gene would be expressed. Such a mouse could be treated with an FK analogue at any time in its life and the caspase would be activated in any tissues that had expressed the gene in question at an earlier time point; once recombination has occurred, the caspase monomer would be expected to be expressed in the cell for the rest of the cell's lifetime. In a model that used Cre recombinase to induce apoptosis immediately, cell types that express Cre in the embryo would be killed and the mice would likely not be viable models. Since many tissue specific genes are known from embryonic development, and numerous Cre mice that express these genes are available, this is a significant avenue for development of disease models and models for the study of pathways by cell ablation.

In general, the transgenic animals described herein can be made by constructing a vector in which a conditional-STOP cassette is placed in the sequence upstream of a dimerizable caspase; the order in which the construct is made is unimportant, so that, for example, the dimerizing sequence can equally be added to a caspase-encoding sequence that already contains a conditional-STOP cassette. The conditional-STOP cassette and dimerizable caspase are placed under the control of a promoter, e.g., a strong ubiquitous or tissue-specific promoter. The resulting vectors are injected into the pronucleus of a fertilized oocyte and used for generation of a transgenic animal with the conditional-STOP dimerizable caspase expressed in all cells in which the promoter is active. This animal can be crossed with a transgenic recombinase-expressing animal to create a new animal in which the caspase is expressed only where and when the recombinase is expressed. For example, crossing with an animal that expresses a recombinase under the control of a promoter from a cell-type specific gene will allow the targeted deletion of a cell type that is characterized by expression of the gene that is normally driven by the promoter that was used for Cre expression.

In at least some of the animals generated using the methods described herein, transgene expression may not be uniform throughout the animals. As described in Example 3, below, variable transgene expression was seen in three lines of animals. This variability of transgene expression among different lines can be used as a "second gate-keeper" for tissue/cell-type specific expression. Therefore, the methods can include selecting a mouse line expressing the dimerizable caspase in the desired cells or tissues. Final expression pattern of FKBP-Caspase monomer is defined by the intersection of Cre recombinase and the CMV promoter-derived dimerizable caspase transgene.

Transgenic Animals and Methods of Use

In one aspect, the invention provides non-human transgenic animals having conditional-STOP dimerizable caspase transgene constructs integrated into their genome. In some embodiments, the transgenes make use of the Cre-lox system or the Flp-FRT system.

A "transgenic animal" is a non-human animal, such as a mammal, generally a rodent such as a rat or mouse, in which one or more of the cells of the animal includes a transgene as described herein. Other examples of transgenic animals include non-human primates, sheep, dogs, cows, goats, chickens, amphibians, and the like. A "transgene" is exogenous DNA that is integrated into the genome of a cell from which a transgenic animal develops and thus remains in the genome of the mature animal, thereby directing the expression of an encoded gene product in one or more cell types or tissues of the transgenic animal. Knock-in animals, which include a gene insertion, are included in the definition of transgenic animals.

A "conditional-STOP cassette" as used herein refers to a construct that features recombinase recognition sequences flanking a coding and polyadenylation signal, e.g., a coding sequence for a protein, preferably a non-toxic protein, e.g., a reporter protein, inserted downstream of a promoter and upstream of the coding sequence of a dimerizable caspase fusion protein, so as to prevent expression of the dimerizable caspase in the absence of a recombinase. The promoter instead drives expression of the reporter protein, and transcription is stopped by the polyadenylation signal. Excision of the conditional-STOP cassette removes the polyadenylation and coding region, and allows the caspase to be expressed from the upstream promoter. The transgene is generally integrated into or occurs in the genome of the cells of a transgenic animal. A "recombinase recognition sequence" as used herein refers to a sequence that directs the recombinase-mediated excision or rearrangement of DNA. Such sequences include lox and FRT sequences, as known in the art and described herein (the term "floxed," as used herein, refers to a pair of lox sequences that flank a region to be excised, in this case, a stop sequence. Although "flox" generally refers to a flanking pair of LoxP sequences, in the present application the term "flox" or "floxed" is used to refer to any flanking pair of recombinase recognition sequences including any lox or FRT sequences.

The conditional-STOP cassette can be used to express the dimerizable caspase fusion protein in one or more cell types or tissues of the transgenic animal in the presence of the Cre or Flp recombinase; expression of the recombinase in a cell harboring the conditional stop transgene results in excision of the sequence encoding the non-toxic protein, e.g., the reporter protein, and its polyadenylation signal, and expression of the dimerizable caspase fusion protein. Thus, a transgenic animal as described herein is one in which at least one copy of a conditional-STOP dimerizable caspase fusion protein has been introduced into a cell of the animal, e.g., an embryonic cell of the animal, prior to development of the animal. A line of transgenic animals (e.g., mice, rats, guinea pigs, hamsters, rabbits, or other mammals) can be produced bearing a transgene encoding a conditional-STOP dimerizable caspase fusion protein in some or all of their cells. Methods known in the art for generating such transgenic animals would be used, e.g., as described below.

The use of the Cre-lox system to direct site-specific recombination in cells and transgenic animals is described in Orban et al., Proc. Natl. Acad. Sci. USA 89(15):6861-5 (1992); Akagi et al., Nuc. Acids Res. 25(9):1766-1772 (1997); Lakso et al., Proc. Natl. Acad. Sci. USA 89:6232-6236 (1992); Rossant and McMahon, Genes Dev. 13(2)142-145 (1999); Wang et al., Proc. Natl. Acad. Sci. USA 93:3932-3936 (1996). The use of the Flp-FRT system to direct site-specific recombination in transgenic animals is described in U.S. Ser. No. 08/866,279, Publication No. U.S. 2002/0170076; Vooijs et al., Oncogene. 17(1):1-12 (1998); Ludwig et al., Transgenic Res. 5(6):385-95 (1996); and Dymecki et al., Dev. Biol. 201 (1):57-65 (1998). Methods known in the art for producing transgenic animals can be used to generate an animal, e.g., a mouse, that bears one conditional dimerizable caspase fusion protein "allele." Two such heterozygous animals can be crossed to produce offspring that are homozygous for the conditional dimerizable caspase fusion protein allele, i.e., have the sequence encoding the dimerizable caspase fusion protein integrated into both copies of a chromosome.

For example, in one embodiment, a suitable vector including a sequence encoding the conditional-STOP dimerizable caspase is introduced into a cell, e.g., a fertilized oocyte or an embryonic stem cell. Such cells can then be used to create non-human transgenic animals in which said sequences have been introduced into their genome. These animals can then in turn be bred with other transgenic animals that express a recombinase, e.g., under the control of a cell-, tissue-, or timing-specific promoter, e.g., a promoter that will turn on expression of the caspase in a specific cell or tissue, or at a specific time in development. Expression of a recombinase in the cell or tissue will result in excision of the stop sequence and allow the conditional dimerizable caspase fusion protein to be expressed. Administration of a dimerizing agent, e.g., FK506 or an analog thereof, to the animal will then cause dimerization of the caspase fusion protein, activating it and initiating apoptosis in the cells. Such animals are useful for studying the effects of cell death in specific tissues, in both young and adult mammals.

Methods for generating transgenic animals, particularly animals such as mice, via embryo manipulation and electroporation or microinjection of pluripotent stem cells or oocytes, are known in the art and are described, for example, in U.S. Pat. Nos. 4,736,866 and 4,870,009, U.S. Pat. No. 4,873,191, U.S. Ser. No. 10/006,611, "Transgenic Mouse Methods and Protocols (Methods in Molecular Biology)," Hofker and van Deursen, Editors (Humana Press, Totowa, N.J., 2002); and in "Manipulating the Mouse Embryo," Nagy et al., Editors (Cold Spring Harbor Laboratory Press, Cold Spring Harbor, N.Y., 2002), which are incorporated herein by reference in their entirety. Methods similar to those used to create transgenic mice can be used for production of other transgenic animals.

In general, in the present methods, a transgenic mouse as described herein is made by injecting a vector made as described herein into the pronucleus of a fertilized mouse oocyte and used for generation of a transgenic mouse with the inducible caspase expressed in all cells, using standard transgenic techniques, e.g., as described in "Transgenic Mouse Methods and Protocols (Methods in Molecular Biology)," Hofker and van Deursen, Editors (Humana Press, Totowa, N.J., 2002); U.S. Pat. Nos. 4,736,866 and 4,870,009, U.S. Pat. Nos. 4,873,191 and 6,791,006, and in Hogan, "Manipulating the Mouse Embryo," Nagy et al., Editors (Cold Spring Harbor Laboratory Press, Cold Spring Harbor, N.Y., 2002).

A transgenic founder animal can be identified based upon the presence of the conditional dimerizable caspase fusion protein transgene in its genome, for example by detecting the presence of the recombinase recognition sequences (e.g., lox or FRT), or by detecting the presence of the FKBP. Founder animals can also be identified by detecting the presence or expression of the conditional-STOP dimerizable caspase fusion protein mRNA in tissues or cells of the animals in the presence and/or absence of recombinase, e.g., Cre or Flp. For example, fibroblasts can be used, such as embryonic fibroblasts or fibroblasts derived from the post-natal animal, e.g., the ear of the post-natal animal. A transgenic founder animal can then be used to breed additional animals carrying the transgene. Moreover, transgenic animals carrying a conditional-STOP dimerizable caspase fusion protein transgene can further be bred to other transgenic animals carrying other transgenes. For example, as noted above, such conditional-STOP dimerizable caspase transgenic animals can be bred to animals expressing a suitable recombinase, e.g., a recombinase under the control of a selected promoter, e.g., a cell-, tissue-, or timing-specific promoter, to induce the apoptosis of specific cells or tissues, e.g., at a specific time.

Once a mouse is obtained that contains the dimerizable conditional-STOP caspase fusion protein transgene in some or all of its somatic and germ cells, this mouse can be crossed with a mouse expressing a suitable recombinase to create a new mouse in which the caspase is expressed, e.g., in a cell type of choice. This will then allow the targeted and conditional deletion of a cell type that is characterized by expression of the gene that would be driven by the promoter that was used for Cre expression, in the presence of a dimerizing agent, e.g., FK506 or an analog thereof.

Vectors

In another aspect, the invention includes, vectors, preferably expression vectors, containing a nucleic acid encoding a dimerizable conditional-STOP caspase fusion protein as described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a nucleic acid encoding a dimerizable conditional-STOP caspase fusion protein in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce the dimerizable conditional-STOP caspase fusion protein, encoded by nucleic acids as described herein.

The recombinant expression vectors described herein can be designed for expression of dimerizable conditional-STOP caspase fusion proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, "Gene Expression Technology: Methods in Enzymology 185," Academic Press, San Diego, Calif. (1990). Alternatively, the recombinant expression vector can be transcribed and translated in vitro, for example using T7 promoter regulatory sequences and T7 polymerase. When used in mammalian cells, the expression vector's control functions are often provided by viral regulatory elements. For example, commonly used promoters are derived from polyoma, Adenovirus 2, cytomegalovirus and Simian Virus 40.

In some embodiments, the invention includes recombinant mammalian expression vectors that are capable of directing expression of the nucleic acid encoding a dimerizable conditional-STOP caspase fusion protein preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) Science 249:374-379) and the α-fetoprotein promoter (Campes and Tilghman (1989) Genes Dev. 3:537-546).

Cells

In another aspect, the invention provides isolated cells that include a nucleic acid molecule as described herein, e.g., a nucleic acid molecule encoding a dimerizable conditional-STOP caspase fusion protein within a recombinant expression vector, or a nucleic acid molecule containing sequences that allow it to homologously recombine into a specific site of the host cell's genome. The terms "host cell" and "recombinant host cell" are used interchangeably herein. Such terms refer not only to the particular subject cell that was contacted with a nucleic acid molecule (e.g., a vector as described herein), but to the progeny or potential progeny of such a cell that also contain the nucleic acid molecule. Because certain modifications may occur in succeeding generations due to either mutation or environmental influences, such progeny may not, in fact, be identical to the parent cell, but are still included within the scope of the term as used herein so long as they also contain the nucleic acid molecule.

A host cell can be any prokaryotic or eukaryotic cell. For example, the cell can be a bacterial cell such as *E. coli*, insect cells, yeast or mammalian cells (such as Chinese hamster ovary cells (CHO), HEK, or COS cells). Other suitable host cells are known to those skilled in the art. Where the vector is a viral vector that can be produced from recombinant cells, e.g., retroviral vectors, the cells can be those that produce the viral vector.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. In some embodiments, naked DNA is simply applied to a cell. Where the vector is a viral vector, known infection protocols can be used.

For example, retroviral vectors can be used, e.g., as described in Robertson et al., Nature 323:445-448 (1986). Retroviruses generally integrate into the host genome with no rearrangements of flanking sequences, which is not always the case when DNA is introduced by microinjection or other methods.

Cells of the present invention also include those cells obtained from the transgenic animals described herein, e.g., cells from the tissues of those animals, that contain the nucleic acid molecule.

Identity of Sequences

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence (e.g., an FKBP sequence shown in FIG. 4) aligned for comparison purposes is at least 80% of the length of the reference sequence, and in some embodiments is at least 90%, 95% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For the present methods, the percent identity between two amino acid sequences is determined using the Needleman and Wunsch ((1970) J. Mol. Biol. 48:444-453) algorithm, which has been incorporated into the GAP program in the GCG software package (available on the world wide web at gcg.com), using the default parameters, i.e., a Blossum 62 scoring matrix with a gap penalty of 12, a gap extend penalty of 4, and a frameshift gap penalty of 5.

Caspases

The cysteine-aspartic acid proteases (caspase) are a family of related proteins, sequential activation of which plays a central role in the execution phase of apoptosis. Caspases exist as inactive proenzymes which undergo proteolytic processing at conserved aspartic residues to produce two subunits, large and small, that dimerize to form the active enzyme. Caspase 3 cleaves and activates caspases 6, 7 and 9, and the protein itself is processed by caspases 8, 9 and 10.

Caspase 3

Alternative splicing of the Caspase 3 gene results in two transcript variants that encode the same protein. The sequence of the longer human caspase 3 preproprotein variant can be found at GenBank Acc. Nos. NM_004346.3 (nucleic acid) and NP_004337.2 (amino acid); the sequence of the shorter variant (beta), which differs in the 5' UTR, is at NM_032991.2 (nucleic acid) and NP_116786.1 (amino acid).

Caspase 8

Caspase 8 is involved in the programmed cell death induced by Fas and various apoptotic stimuli. A number of isoforms exist as a result of alternative splicing, including:

| Nucleic acid | Amino acid | Name | Description |
| --- | --- | --- | --- |
| NM_001228.4 | NP_001219.2 | caspase 8 isoform A precursor | Variant (A), also known as Alpha-4, has multiple differences in the 5' UTR and coding region, compared to variant G. It encodes isoform A which is shorter than isoform G. |
| NM_033355.3 | NP_203519.1 | caspase 8 isoform B precursor | Variant (B) includes different segments in its 5' UTR and lacks a 5' coding region segment, compared to variant G. This results in translation at a downstream start codon, and the encoded protein (isoform B) has a shorter N-terminus when it is compared to isoform G. |
| NM_033356.3 | NP_203520.1 | caspase 8 isoform C precursor | Variant (C) includes a different segment in the 5' UTR and lacks an alternate in-frame segment in the coding region, compared to variant G. Variants C and F both encode isoform C, which is shorter than isoform G. Isoform C has also been labelled as Alpha-2 or MCH5-beta. |
| NM_033358.3 | NP_203522.1 | caspase 8 isoform E | Variant (E), also known as Beta-1, has multiple differences, one of which causes a frameshift, compared to variant G. It encodes isoform E, which is shorter than isoform G. |
| NM_001080124.1 | NP_001073593.1 | caspase 8 isoform C precursor | Variant (F) includes different segments in the 5' UTR and lacks an alternate in-frame segment in the coding region, compared to variant G, but variants C and F both encode isoform C, which is shorter than isoform G. |
| NM_001080125.1 | NP_001073594.1 | caspase 8 isoform G precursor | Variant (G), also known as procaspase-8L or 8L, encodes the longest protein (isoform G). |

Caspase 9

Caspase 9 also has multiple isoforms resulting from alternative splicing. The alpha transcript variant (NM_001229.2, caspase 9 isoform alpha preproprotein) represents the longer transcript and encodes the longer isoform (alpha, NP_001220.2). The beta variant (NM_032996.1 caspase 9 isoform beta preproprotein) lacks several exons in the coding region but maintains the reading frame, compared to variant alpha. It encodes isoform beta (NP_127463.1) which is shorter than isoform alpha. Isoform beta lacks protease activity and acts as an apoptosis inhibitor, and is therefore not suitable for use in methods intended to produce an apoptotic response.

Thymidine Kinase

TK can also be used, e.g., thymidine kinase 1, soluble, the sequence for which is NM_003258.3 (nucleic acid), which encodes NP_003249.2 (amino acid)

FK Binding Proteins and Variants

FK506 binding proteins (FKBPs) are abundant and relatively ubiquitous cytosolic proteins, members of the peptidyl-prolyl cis-trans isomerases (PPIases), which catalyze cis-trans conversions about Xaa-Pro bonds. FKBPs are a receptor for immunosuppressant macrolides rapamycin, FK506, and FK1706. FKBPs range in size from 12 kDa to 135 kDa. For the purposes of the present methods, the 12 kDa FKBPs, referred to as FKBP1 and/or FKBP12, are preferred; in particular, the variant of FKBP12 engineered to bind AP20187 is preferred (see, e.g., Clackson et al., Proc. Natl. Acad. Sci. USA 95: 10437-10442 (1998); vectors and sequences commercially available from Ariad Pharmaceuticals, Inc., Cambridge, Mass.). FKBP1 has also been referred to as protein kinase C inhibitor-2 (PKCI2).

In mammalian systems, there are two isoforms of FKBP1. The sequences are available in GenBank under Acc. Nos. NM_054014.1 (nucleic acid) and NP_463460.1 (amino acid) for a shorter mRNA form; and NM_000801.2 (nucleic acid) and NP_000792.1 (amino acid) for a longer mRNA form. A sequence alignment of FKBP1 from *Bos Taurus, Rattus norvegicus, Mus musculus, Macaca mulata, Pan troglodytes* and *Homo sapiens* appears in FIG. 4.

Other FKBPs are known in the art, e.g., FKBP12.6, and FKBP51. See, e.g., Weiwad et al., Biochemistry, 45(51): 15776-15784 (2006).

Figure 4:
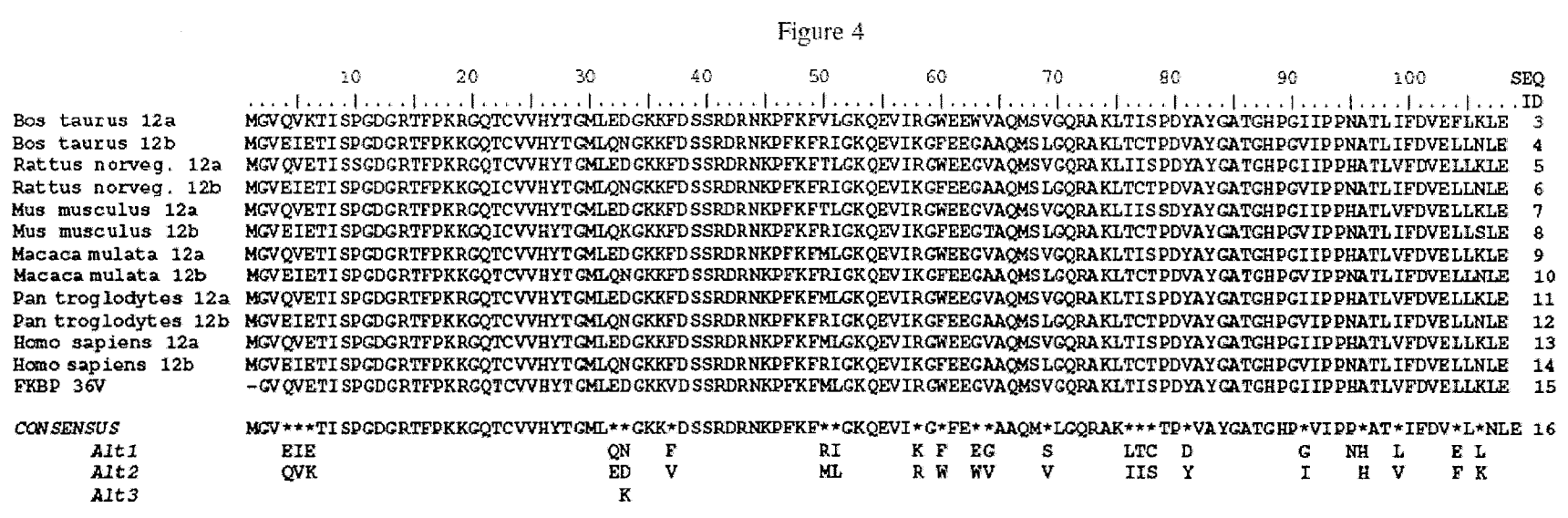

The transgene constructs described herein comprise a sequence encoding an FKBP or a variant thereof. In some embodiments, the FKBP is a wild-type FKBP, e.g., a mammalian sequence as shown in FIG. 4. In some embodiments, the constructs described herein are made using a sequence that is at least 80% identical to a sequence that appears in FIG. 4, e.g., at least 90%, 92%, 94%, 95%, 97%, 98%, or 99% identical. In some embodiments the sequence used differs by at least one but by less than 30, 25, 20, 15, 10 or 5 amino acid residues. In some embodiments, it differs from the corresponding sequence in FIG. 4 by at least one residue, but less than 20%, 15%, 10% or 5% of the residues in it differ from the corresponding sequence in FIG. 4.

In general, any and all substitutions will be conservative substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, and histidine), acidic side chains (e.g., aspartic acid, and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), beta-branched side chains (e.g., threonine, valine, and isoleucine) and aromatic side chains (e.g., tyrosine, phenylalanine, tryptophan, and histidine).

All variants useful in the methods described herein will retain the ability to bind a dimerizing agent as described herein, e.g., FK506, and the ability to dimerize in response to binding of such an agent.

A consensus sequence appears at the bottom of FIG. 4. Those amino acids which are important in function of FKBP are known in the art, see, e.g., Somarelli and Herrera, Biol. Cell. 99(6):311-21 (2007). FIG. 4 also provides the sequences of additional FKBP1s from various other species.

Figure 3A:
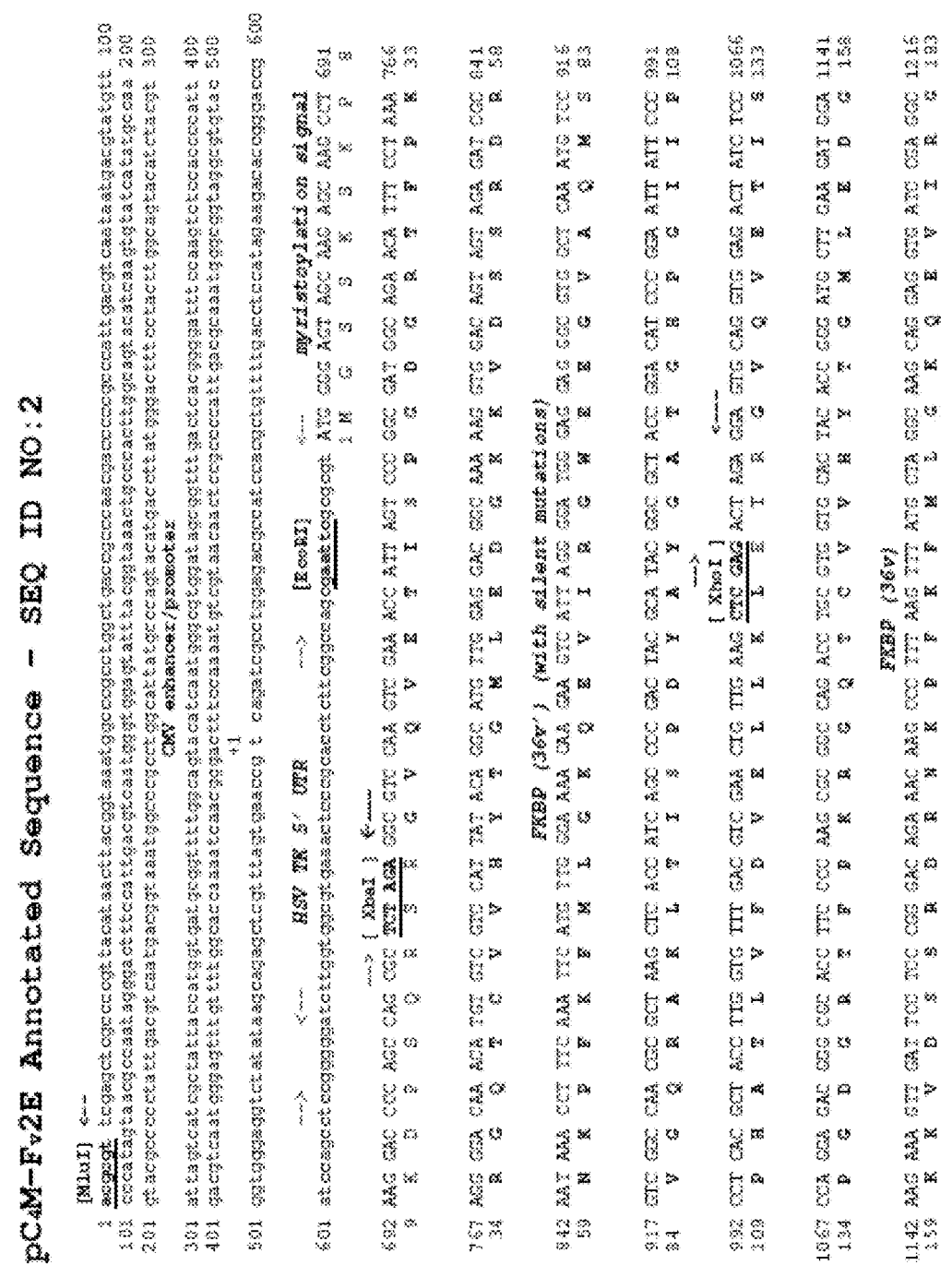
Figure 3B:
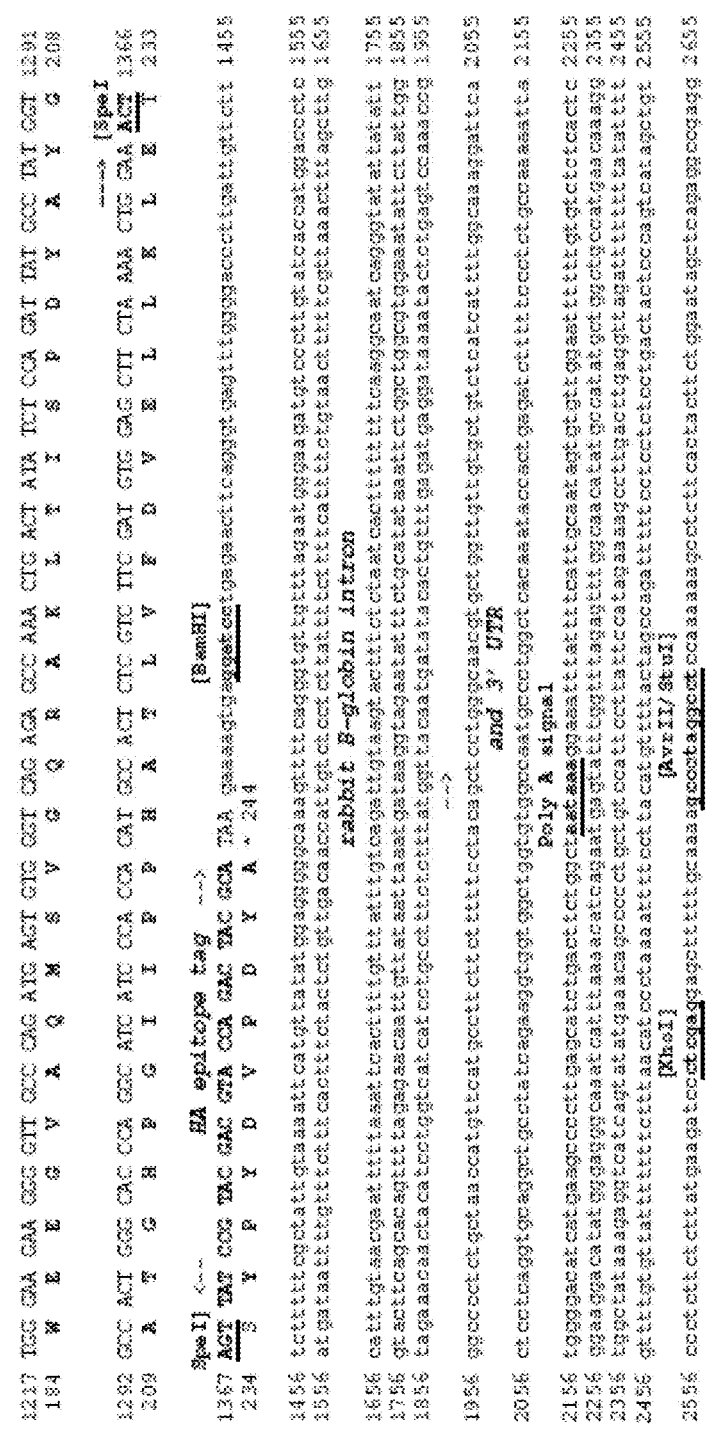

Methods for constructing transgenes useful in the present methods are known in the art; see, e.g., Sambrook and Russell, "Molecular Cloning: A Laboratory Manual," Cold Spring Harbor Laboratory Press; 3rd Labman edition (Jan. 15, 2001); and Ausubel et al., Eds., "Short Protocols in Molecular Biology," Current Protocols; 5 edition (Nov. 5, 2002). In some embodiments, commercially-available vectors can be used in constructing the nucleic acid molecules described herein, e.g., pC4M-Fv2E (available from Ariad Pharmaceuticals, Cambridge, Mass.). In some embodiments, more than one FKBP will be fused in frame with the caspase. For example, two, three, or more FKBP can be used. The vector pC4M-Fv2E (available from Ariad Pharmaceuticals, Cambridge, Mass.), a partial sequence of which is shown in FIG. 3, can be used to produce a fusion protein with two FKBPs fused in frame with the caspase.

FKBP Dimerizing Agents

The methods described herein include the use of FKBP dimerizing agents to induce dimerization, and thus activation, of the dimerizable conditional-STOP caspase fusion proteins described herein.

A number of suitable FKBP dimerizing agents are known in the art. These agents include FK506, rapamycin, and analogs of rapamycin or FK506.

Analogs of FK506 include, e.g., substituted 5,5-dimethyl-2-(4-thiazolidine)carboxylates, polycyclic aza-amide analogs, aza-proline and aza-pipecolic acid analogs. Specific analogs include L-685818, (R)- and (S)-[18-OH]ascomycin, 3-(3-pyridyl)-1-propyl (2S)-5,5-dimethyl-1-(3,3-dimethyl-1,2-dioxobutyl)-2-(4-thiazolidine)carboxylate), FK1706, FK1012, GPI-1046 and non-cyclic derivatives of GPI-1046, A-119435, and AP1510. See, e.g., Petros et al., FEBS Lett. 308(3):309-314 (1992); Hudak et al., J Med Chem. 49(3): 1202-6 (2006); Zhao et al., J Med Chem. 49(14):4059-71 (2006); Zhao et al., Bioorg Med Chem Lett. 16(16):4385-90 (2006); Fujitani et al., J Chem Phys. 123(8):084108 (2005); Mollison et al., J. Pharm. Exp. Ther. 283(3):1509-1519 (1997); and Wilkinson et al., Bioorg. Med. Chem. 11:4815-4825 (2003). For FK506 and analogous fermentation products, see also, e.g., U.S. Pat. No. 4,894,366 and the more recent WO 04/78167.

Analogs of rapamycin include C-43-modified rapamycin analogs, e.g., AP23573 (see WO 03/064383), temsirolimus (CC1779, see WO 2004/026280), everolimus (U.S. Pat. No. 6,384,046 and references cited therein), and ABT-578 (a rapamycin derivative bearing a tetrazole moiety in place of the OH at position 43, see US PGPub No. 20060194829); see also US PGPub Nos. 20060194829, 20060078980, and 20050272132. Additional rapamycin analogs are known in the art, see, e.g., WO 01/144387; WO 97/10502; WO 94/18207; WO 93/04680; U.S. Pat. No. 5,527,907; U.S. Pat. No. 5,225,403; WO 96/41807; WO 94/10843; WO 92/14737; U.S. Pat. No. 5,484,799; U.S. Pat. No. 5,221,625; WO 96/35423; WO 94/09010; WO 92/05179; U.S. Pat. No. 5,457, 194; U.S. Pat. No. 5,210,030 WO 96/03430 WO 94/04540; U.S. Pat. No. 5,604,234; U.S. Pat. No. 5,457,182; U.S. Pat. No. 5,208,241; WO 96/00282; WO 94/02485; U.S. Pat. No. 5,597,715; U.S. Pat. No. 5,362,735; U.S. Pat. No. 5,200,411; WO 95/16691; WO 94/02137; U.S. Pat. No. 5,583,139; U.S. Pat. No. 5,324,644; U.S. Pat. No. 5,198,421; WO 95/15328; WO 94/02136; U.S. Pat. No. 5,563,172; U.S. Pat. No. 5,318, 895; U.S. Pat. No. 5,147,877; WO 95/07468; WO 93/25533; U.S. Pat. No. 5,561,228; U.S. Pat. No. 5,310,903; U.S. Pat. No. 5,140,018; WO 95/04738; WO 93/18043; U.S. Pat. No. 5,561,137; U.S. Pat. No. 5,310,901; U.S. Pat. No. 5,116,756; WO 95/04060; WO 93/13663; U.S. Pat. No. 5,541,193; U.S. Pat. No. 5,258,389; U.S. Pat. No. 5,109,112; WO 94/25022; WO 93/11130; U.S. Pat. No. 5,541,189; U.S. Pat. No. 5,252, 732; U.S. Pat. No. 5,093,338; WO 94/21644; WO 93/10122; U.S. Pat. No. 5,534,632; U.S. Pat. No. 5,247,076; and U.S. Pat. No. 5,091,389.

In addition, a new generation of FKBP dimerizing agents has been developed that do not bind to the native FKBPs, but bind with high affinity to FKBPs with a single amino acid substitution: Phe36Val; see SEQ ID NO:15. These new agents include AP1889, AP1903 and AP20187. Additional information regarding these reagents can be found in the art, including in the following references: Spencer et al., Science 262:1019-24 (1993); Amara et al., Proc Natl Acad Sci USA 94:10618-23 (1997); Clackson et al., Proc Natl Acad Sci USA 95:10437-42 (1998); and Pollock and Rivera, Methods Enzymol 306: 263-81 (1999).

Finally, numerous additional agents are listed in U.S. Pat. Pub. No. 2006/0194829, 2006/0078980, and 20050272132.

In a preferred embodiment, the dimerizing agent is AP20187, available from Ariad. In mice, a 0.5-10 mg/kg dose of AP20187 delivered i.p. will generally give a good response, but a range of concentrations (e.g., from 0.005 to 10 mg/kg) is also recommended to find the lowest effective dose.

Conditional-STOP Cassettes

In the conditional-STOP dimerizable caspase constructs described herein, a conditional-stop cassette is included that prevents expression of the downstream caspase. The cassette includes a first recombinase recognition site, a cDNA encoding a protein, at least one polyadenylation signal to stop transcription, and a second recombinase recognition site. In some embodiments, the protein is a non-toxic protein, e.g., a reporter protein, e.g., lacZ (which encodes beta-galactosidase); luciferase; a fluorescent protein, such as green fluorescent protein (GFP), red FP (RFP), yellow FP (YFP), or a variant thereof, or V5. A "non-toxic" protein is a protein that, when expressed in a cell, is not generally associated with significant cell death. Preferably the protein will not have a significant effect on cell function or physiology. Expression of the protein is driven by the promoter included in the construct, and the presence of the polyadenylation signal prevents transcription of the downstream caspase until a recombinase excises the cassette including the protein and polyadenylation signal, after which the caspase is expressed. See, e.g., Moeller et al., Am. J. Physiol. Renal. Physiol. 289 (2):F481-8 (2005). The protein and the dimerizable caspase are not the same protein.

Recombinase-Expressing Transgenic Mice

Once a mouse is obtained that contains the transgene in all of its somatic and germ cells, this mouse can be crossed with any mouse with cell or tissue-specific expression of a recombinase, e.g., Cre or Flp, to create a new mouse in which the caspase is expressed in a cell type of choice. This will then allow the targeted and conditional deletion of a cell type that is characterized by expression of the gene that would be driven by the promoter that was used for Cre expression, in the presence of the dimerizing agent, e.g., FK506.

Hundreds of recombinase-expressing mice have been described and are commercially available; for example, Jackson Laboratory of Bar Harbor, Me., lists over 200 such mice on their website. A few examples include the strain B6.Cg-Tg(Camk2a-cre)T29-1Stl/J. These transgenic mice express the Cre recombinase under the control of the mouse calcium/calmodulin-dependent protein kinase II alpha promoter. Cre recombinase is expressed only in the forebrain, specifically in the CA1 pyramidal cell layer in the hippocampus. When crossed with a strain containing loxP site flanked sequence of interest, Cre-mediated recombination occurs in the pyramidal cell layer. Another strain, FVB-Tg(Ckmm-cre)5Khn/J, have a cre recombinase gene driven by the muscle creatine kinase (MCK or Ckm) promoter. Cre activity is observed in skeletal and cardiac muscle. Inner hair cell Cre-expressing transgenic mice are described in Li et al., Genesis 39(3):173-7 (2004) and Tian et al., Dev Dyn. 231(1):199-203 (2004); Pirvola et al., Neuron 35(4):671-80 (2002), and Chow et al., Dev Dyn. 235(11):2991-8 (2006).

Other inner ear-specific genes include Ngn1 (neurogenin 1), islet1, Gata3 (neurons), Math1 (hair cells), and Prox1, Sox2, and musashi (supporting cells).

In some embodiments, the methods described herein can be used with mice that express a recombinase in one or more selected cell types or organs, e.g., selectively in one or more cell types of the brain, ear, skin, connective tissue, muscle, bone, and/or internal organ(s), e.g., heart, lungs, liver, kidneys, or pancreas.

Double transgenic mice obtained by breeding $F_1$ transgenic mice generated as described herein Example 3 can be crossed using standard breeding methods with selected Cre-expressing mice, e.g., Insulin-Cre: Diabetes model (targeting islet cells)

keratin15-Cre: Baldness model (targeting hair follicle stem cells)

pou4f3-Cre (also know as Brn3c): Hearing loss model (targeting cochlear sensory cell)

ngn1-CreER (neurogenin): Hearing loss model (targeting ganglion neurons) (Jackson Labs)

TTR-Cre (transthyretin): (targeting hepatocytes) (see, e.g., Mallet et al., Nat. Biotech. 20:1234-1239 (2002)

Rosa26-CreER: ubiquitous, for in vitro experiments

For example, crossing the STOP-flox-caspase3 mice to a Kr15-Cre mouse will make the hair cell follicles susceptible to FK506 analogue induced cell death. A number of Cre-expressing mice are available commercially, e.g., from Jackson Labs, Bar Harbor, Me.

Most degenerative diseases begin with gradual and incomplete loss of specific cell types, yet the models for "onset" of these diseases have not fully been established. Moderate but low-variation cell ablation is technically difficult when the model is created either by drug treatment or gene manipulation. The present mouse model successfully recapitulates the partial loss of cells typically seen in degenerative diseases: mosaic-patterned stochastic cell ablations within specific cell types.

In some embodiments, the methods described herein can be used to create mice that are models of genetic diseases with single or multiple gene defects that lead to loss of one or several cell types, e.g., Huntington's disease or Parkinson's disease (e.g., using one or more Cre recombinases that target dopaminergic cells, e.g., in the substantia nigra, e.g., as described in Lemberger et al., BMC Neuroscience, 8:4 (2007), or under the control of a tyrosine hydroxylase gene 3' UTR, e.g., as described in Lindeperg et al., Genesis, 40(2): 67-73 (2004)), and muscular dystrophy (e.g., using a dystrophin-promoter driven Cre). In some embodiments, the disease is a later-onset disease, e.g., adult-onset. Additional exemplary mouse models and diseases include: Insulin-Cre: Diabetes model (targeting islet cells); keratin15-Cre: Baldness model (targeting hair follicle stem cell); pou4f3-Cre: Hearing loss model (targeting cochlear sensory cells); ngn1-CreER: Hearing loss model (targeting ganglion neurons); and Rosa26-CreER: useful for in vitro experiment.

EXAMPLES

The invention is further described in the following examples, which do not limit the scope of the invention described in the claims.

Example 1

Construction of a Conditional-Stop Caspase Vector

This Example describes methods for constructing a vector in which a conditional-STOP cassette is placed upstream of an inducible caspase. The cDNA for the floxed STOP caspase3 was generated by engineering the caspase gene with a FK506 analogue binding site and a myristoylation sequence into a plasmid containing a STOP-flox sequence in conjunction with a LacZ gene (Moeller et al., Am. J. Physiol. Renal Physiol. 289(2):F481-8 (2005)).

A transgene that irreversibly expressed AP20187 (an FK506-analogue)-responsive human myristoylated pro-caspase-3 under the control of a CMV-promoter after co-expression of Cre-recombinase was constructed as follows.

The 1583 bp coding sequence of M-Fv2-Casp3-E was subcloned from pSH1/M-Fv2-Casp3-E (Mallet et al., Nat. Biotech. 20:1234-1239 (2002)) into the pDrive-9 transit plasmid using the QIAGEN PCR cloning kit (QIAGEN). The sequence was confirmed, and a clone in which the amplified gene was inserted in the forward direction was selected (MFv2Casp3E/pDrive-9). The 1.7 Kb KpnI-XbaI fragment of this transit plasmid was cloned into pCMV/flox (Moeller et al., supra) at the respective sites (pCMVfloxMFv2Casp3E; shown in FIG. 1).

The following oligonucleotide primers were used for the PCR: MFv2Casp3E-f: 5'-CCACCATGGGGAGTAGCAA-GAG-3', MFv2Casp3E-r: 5'-GGAATTCTTAGTCGAGT-GCGTAGT-3'.

Example 2

In Vitro Confirmation of Dimerizable Conditional-Stop Caspase Construct

A fusion Caspase-3 derivative gene was subcloned from pSHMFv2Caspase3E by PCR and inserted into the multiple cloning site of pCMVflox as described herein. The resulting plasmid was named pCMVfloxMFv2Csp3E, and the sequence was confirmed.

To confirm that the system works, the effect of the dimerizer, AP20187, was examined in vitro on cells that were transfected with either pCAN-Cre or pCMVflox, or cotransfected with both. 24 hours after transfection, cells were treated with the dimerizer AP20187, and 48 hours later cell-viability/dying cells were examined using a standard MTT (3-(4,5-dimethylthiazol-2-yl)-2,5-diphenyltetrazolium bromide) assay. By MTT assay, cell viability was significantly reduced only in the group where both Cre-recombinase and transgene were transfected (FIG. 6A).

To determine the extent of cell ablation, the co-transfected cells were compared with the original pSHMFv2Caspase3E in the presence of AP20187 using LIVE/DEAD analysis (Invitrogen). The number of dying cells and the decrease in cell viability was almost same in the co-transfected group as compared to the original plasmid transfection group (FIGS. 6B-6C). These results demonstrate that this plasmid works for in vivo spatiotemporal cell ablation.

Example 3

Generation of a Dimerizable Conditional-Stop Caspase Mouse

After microinjection of linearized plasmid into about 30-40 mouse oocytes using standard methods, twenty nine pups were born. The pups were genotyped by PCR, and Select seven male transgenic mice were identified as candidate founders ($F_0$) and bred.

An appropriate line was chosen, using the following criteria ($F_1$ analyses):
1—genotyping PCR
2—protein expression
   a) Whole body scale distribution (this was determined by X-gal staining of whole embryos)
   b) Detailed expression pattern in adults (this is determined, e.g., by beta-gal activity in each organ, using a luminometer, and anti-LacZ staining of each organ of interest)
3—Functional screening
   E.g., in vitro cell-death analyses A summary of the F1 analysis is shown in FIG. 7. The results indicated that lines B, D, and E are the best candidates. Actual expression of the transgene in each of these lines was confirmed by LacZ staining of F1 offspring; the results, shown in Table 1, show that each of these lines was highly positive, though expression was not uniform throughout the animal.

TABLE 1

Transgene Expression in Selected Lines

| Tissue | Transgenic Line B | D | F | wt |
|---|---|---|---|---|
| forebrain | 0.355 | 0.335 | 0.282 | 0.151 |
| brainstem | 0.356 | 0.598 | 0.427 | 0.195 |
| cerebrum | 0.356 | 0.176 | 0.921 | 0.124 |
| spinal cord | 0.553 | 0.288 | 0.287 | 0.211 |
| olfactory bulb | 0.128 | 0.805 | 0.558 | 0.133 |
| eye | 0.308 | 0.19 | 0.64 | 0.208 |
| temporal bone | 0.703 | 0.227 | 0.331 | 0.119 |
| salivary grand | 0.191 | 0.194 | 0.286 | 0.182 |
| tongue | 0.853 | 0.512 | 0.843 | 0.165 |
| lung | 0.399 | 0.232 | 0.255 | 0.368 |
| heart (atrial) | 0.165 | 0.193 | 0.243 | 0.334 |
| heart (ventricle) | 0.277 | 0.324 | 0.652 | 0.193 |
| diaphragm | 0.791 | 0.256 | 0.344 | 0.253 |
| esophagus | 0.234 | 0.144 | 0.755 | 0.511 |
| stomach | 0.14 | 0.355 | 0.547 | 0.113 |
| ileum | 0.204 | 0.182 | 0.302 | 0.122 |
| caecum | 0.166 | 0.154 | 0.156 | 0.18 |
| colon | 0.228 | 0.24 | 0.28 | 0.135 |
| liver | 0.351 | 0.196 | 0.419 | 0.671 |
| spleen | 0.948 | 0.844 | 0.937 | 1.014 |
| pancreas | 0.331 | 0.753 | 0.686 | 0.165 |
| adrenal gland | 0.374 | 0.513 | 0.686 | 0.834 |
| kidney | 0.24 | 0.353 | 0.96 | 0.314 |
| ovary | 0.185 | 0.212 | 0.384 | — |
| testis | — | — | — | 0.176 |
| bladder | 0.175 | 0.153 | 0.189 | 0.491 |
| muscle | 0.809 | 0.259 | 0.826 | 0.303 |
| skin | 0.773 | 0.817 | 1.19 | 0.369 |
| tail | 0.58 | 0.935 | 0.867 | 0.167 |
| Thymus | 0.179 | 0.235 | 0.941 | |
| gallbladder | 0.11 | 0.131 | | |
| uterus | | 0.197 | | |

Example 4

Generation of Double Transgenic Mice

A transgenic mouse with an inducible caspase gene was constructed as described above for targeted cell ablation. Double transgenic mice were obtained by breeding $F_1$ transgenic mice generated as described in Example 3 crossed using standard breeding methods with selected Cre-expressing mice, i.e., Insulin-Cre: Diabetes model (targeting islet cells)
   pou4f3-Cre (also know as Brn3c): Hearing loss model (targeting cochlear sensory cell)
   Rosa26-CreER: ubiquitous, for in vitro experiments For example, crossing the STOP-flox-caspase3 mice to a Krl5-Cre mouse will make the hair cell follicles susceptible to FK506 analogue induced cell death. A number of Cre-expressing mice are available commercially, e.g., from Jackson Labs, Bar Harbor, Me.

Expression of the caspase in cell-specific, time-specific manner is achieved in the mice by administering a dimerizing agent, e.g., AP20187. FIGS. 7A-C illustrate the expression of lac Z (7A) or the transgene (7B-C) in cells where transgene is driven by CMV promoter in the absence (7A) or presence (7B-C) of Cre recombinase. As examples, a pre-diabetic model and a mild hearing loss model were generated; both correlated in vivo to functional deficiency. A mouse with a ubiquitously expressed Cre recombinase was also used (rosa26-CreER), to verify transgene expression and function.

Cross with Cre Recombinase: Rosa26-CreER

Figure 13:
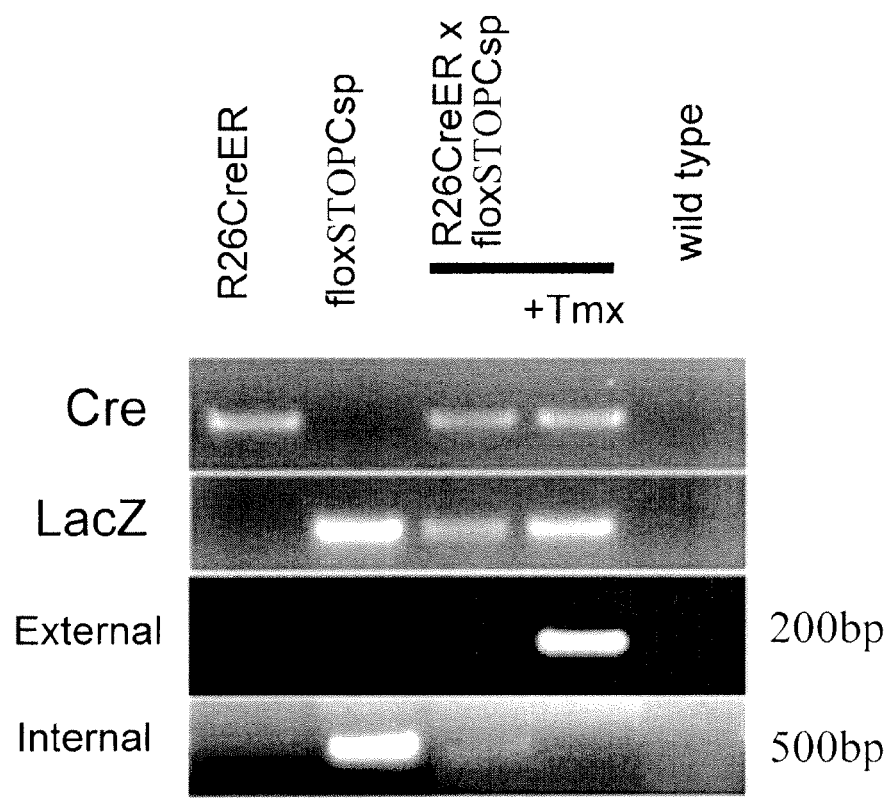
FIG. 13 is a gel showing the presence of Cre in the Cre mouse; lacZ in the line F transgenic mouse; both cre and lac Z, and an unrecombined 500 bp product, in the double transgenic mice, in the absence of tamoxifen (Tmx), while in the presence of tamoxifen the recombined product at 200 bp is present.

To provide a model for ready confirmation of the function of the conditional-stop dimerizable caspase transgene, the transgenic mice described herein (line F) were crossed with Rosa26-CreER mice. In vitro experiments on cells from the mice were contacted with tamoxifen to induce expression of the Cre recombinase, and the results, shown in FIG. 13, indicate successful recombination and expression of the transgene. A band at the expected size in Lane 1 indicates that the Cre mouse expresses Cre, and in Lane 2 demonstrates the presence of lacZ in the line F transgenic mouse. In the double transgenic mice, in the absence of tamoxifen (Tmx), both cre and lac Z are present, as is the unrecombined 500 bp product (lane 3), while in the presence of tamoxifen the recombined product at 200 bp is present. The presence of some lacZ in the double transgenics in the presence of tmx indicates that the recombination is incomplete, which may be due to partial recombination with R26Cre/ER. These results confirm the confirm that in vivo recombination is taking place in the double transgenics.

Figure 2:
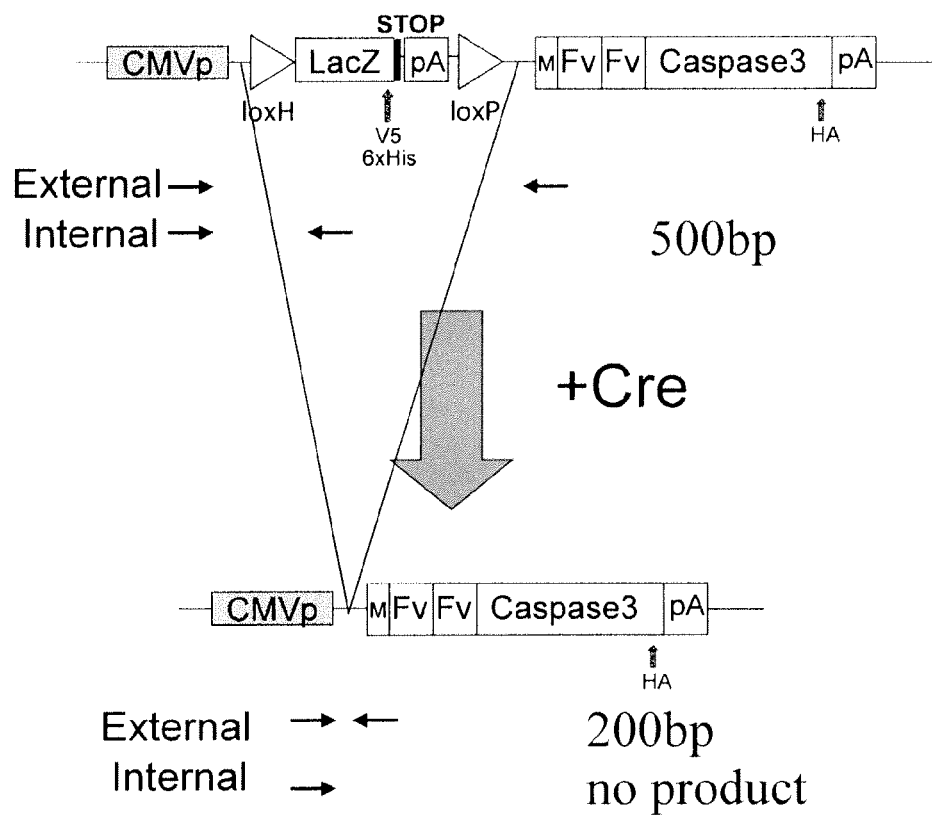
FIG. 2 is a schematic illustration of the genetic processes occurring in the double transgenic mice.
Figure 8A:
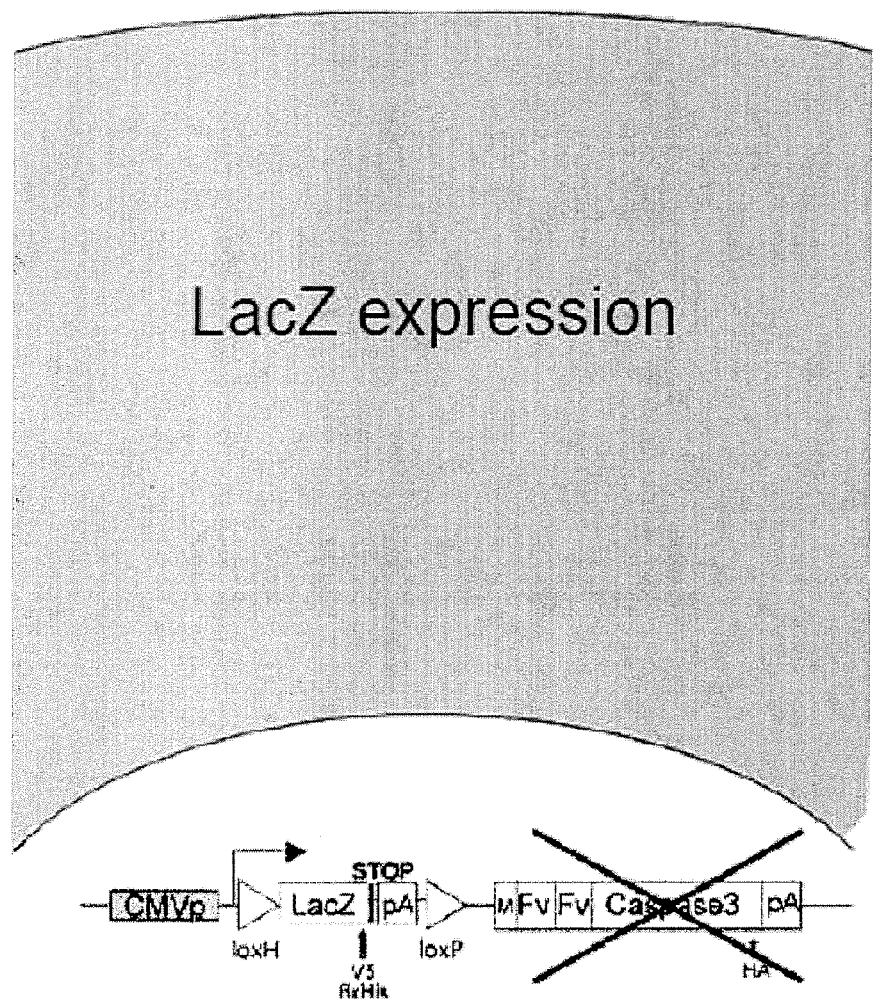

FIG. 2 is a schematic illustration of the genetic processes occurring in the double transgenic mice.

Cross with Cre Recombinase: Brn3c-Cre

Auditory hair cells are the mechanosensory channel that transduce sound waves to action potentials. Since mammalian hair cells cannot spontaneously regenerate once lost, regenerative medicine for hearing loss would be of great importance, and it has been difficult to establish a reproducible model for ablation of hair cells. The transgenic mice described herein (line D) were mated with a hair cell-specific, Brn3c-Cre mouse from Doug Vetter (Xiang et al., Proc. Natl. Acad. Sci. U.S.A. 94(17):9445-50 (1997); Sage et al., Proc. Nat. Acad. Sci. 103(19):7345-7350 (2006)).

Detailed expression pattern in the auditory system including cochlea and brain was also determined by anti-V5 tag immunostaining in each of the three transgenic lines B, D, and F. One of the lines (line B) showed moderate expression in the cochlea, but almost no expression in the brain, while another line (line F) had ubiquitously high expression in the brain and cochlea. A brief summary of transgene expression in auditory systems is shown in Table 2.

TABLE 2

Transgene Expression in Auditory and Brain Tissues of Selected Lines

| | | Tissue | | |
|---|---|---|---|---|
| Line | IHC | OHC | spiral ganglion | brainstem/cortex |
| B | + | + | +++ | −/− |
| D | ++ | + | ± | +/− |
| F | +++ | + | ± | ++/++ |

Inner hair cells (IHC); outer hair cells (OHC).

Thus, line B, D, or F can be chosen for a hair cell loss model (e.g., x Brn3c-Cre), and line B would be the best for a spiral ganglion loss model (e.g., x Ngn1-Cre).

In an in vitro experiment using an organ of Corti explant culture, the double transgenics showed 38.8% inner hair cell loss and 32.4% outer hair cell loss within 24 hours of incubation in the medium containing AP20187 suggesting rapid ablation occurred.

Figure 10A:
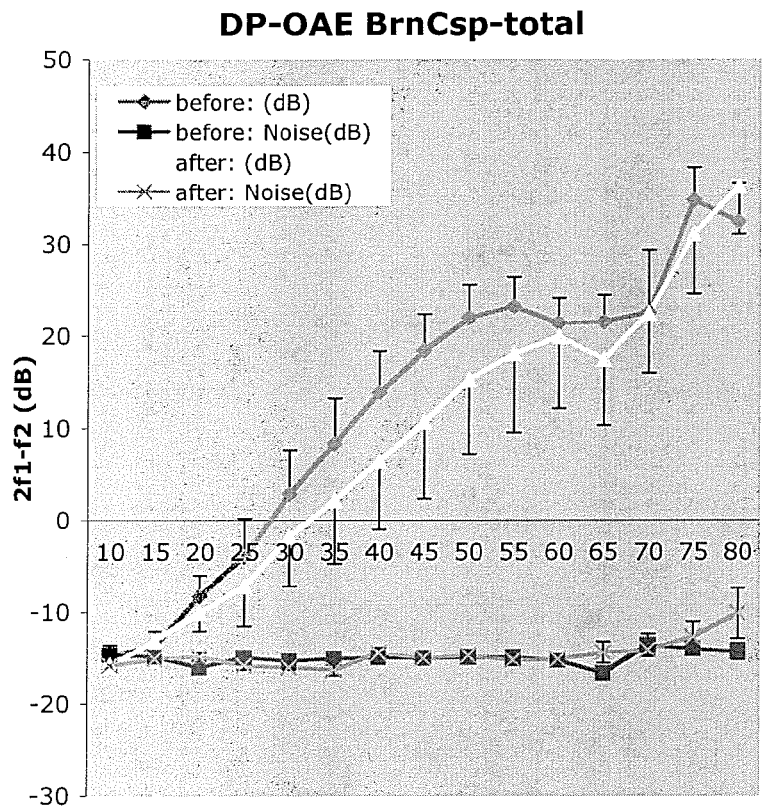
FIG. 10A is a line graph showing changes in DP-OAE after dimerizer administration in Brn3c double Tg animals.
Figure 10B:
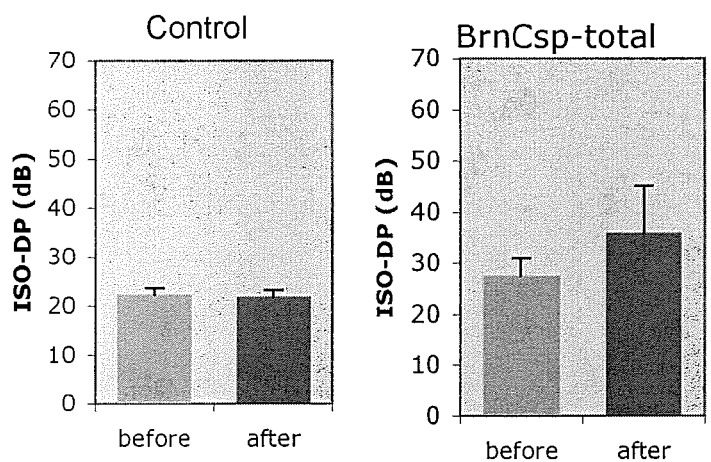
FIG. 10B is a pair of bar graphs showing a significant increase in ISO-DP in treated Brn3c double Tg animals.

In vivo experiments were also performed. Animals at 6-8 weeks of age were administered AP20187 (10 mg/kg ip) and analyzed six days later. A 60% decrease in the amplitude of the auditory brainstem response (ABR) as compared with same-animal measurements taken before treatment was also seen, indicative of hearing loss with 37.8% of inner hair cells lost after drug treatment (see FIGS. 9A-9F). Distortion product otoacoustic emissions (DPOAE), responses generated when the cochlea is stimulated simultaneously by two pure tone frequencies whose ratio is between 1.1 to 1.3, were significantly decreased in the treated animals, see FIG. 10A. ISO-DP, a measure of the threshold required to obtain a given level of response, was significantly increased in treated animals (FIG. 10B). Immunohistochemical experiments were consistent with this result. Mosaic loss of parvalbumin 3 (Pv3, a hair cell marker)-positive hair cells was seen in transgenics after AP20187 administration. Approximately 35~40% of inner hair cells and 15% of outer hair cells were lost, as judged by Pv3 staining. Note that Musashi-1 staining depicts that pharyngeal processes of supporting cells was preserved, demonstrating ablation specifically occurred in hair cells. In addition, areas of dead cells (identified by a lack of Pv3 in hair cell plane) were partially covered by Msi1 staining, suggesting the presence of pharyngeal scarring in response to neighboring hair cell death. No remarkable changes were seen in the spiral ganglion.

Cross with Cre Recombinase: Ins-Cre

Diabetes is cause by loss of insulin producing beta cells in the pancreas. These cells cannot be replaced by known techniques. A model for impaired glucose tolerance was constructed by crossing the transgenic mouse (line B) described herein with an Ins-Cre mouse (Jackson Labs). Partial loss of beta cells resulted in hyperplasia of existing islets of Langerhans and impaired glucose tolerance. This model has the characteristics of a pre-diabetic mouse.

The FK506 analogue AP20187 was administered by intraperitoneal (IP) injection. β-cell death was monitored in the animals by intraperitoneal glucose tolerance testing (IPGTT) using standard methodology. The results, shown in FIG. 11A, demonstrate a partial loss of glucose control in the double transgenic animals treated with the dimerizer, similar to what is seen in humans with glucose intolerance, during the onset of Type 1 diabetes. This effect was more pronounced in female animals than in males, as shown in FIGS. 11B-C.

Figure 12A:
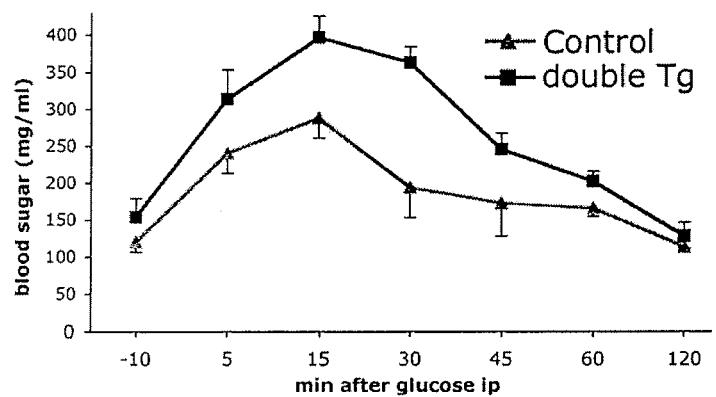
FIG. 12A is a line graph showing the effect of dimerizing agent on blood sugar in Ins-Cre double Tg animals.
Figure 12B:
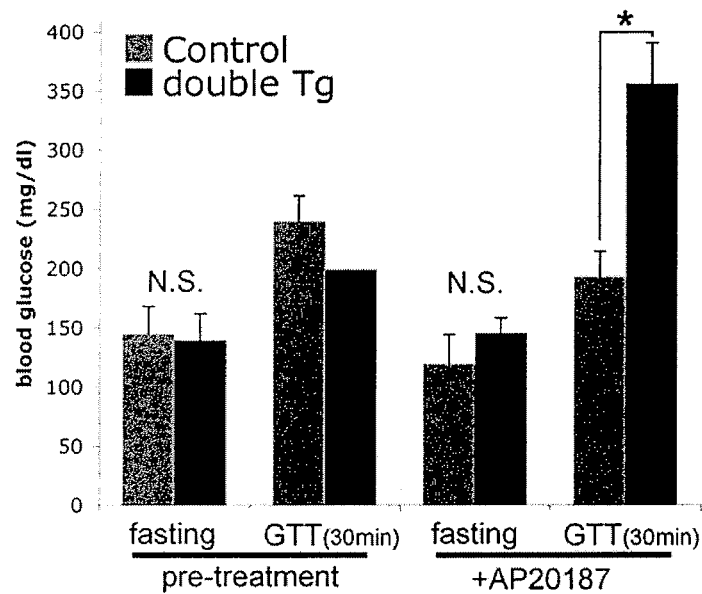
FIG. 12B is a bar graph showing the effect of dimerizing agent on blood sugar in Ins-Cre double Tg animals.

The effect on blood glucose levels was also evaluated using a standard glucose tolerance test (GTT). 30 minutes after a glucose challenge, a blood sample was obtained from the tail vein and a measurement of blood glucose was obtained with a glucose monitor. The results are shown in FIGS. 12A-B, and demonstrate that a significant increased in blood glucose levels was seen.

These results demonstrate that these mice recapitulate the partial loss of cells in the time course of degenerative diseases, and are thus a useful model for the onset of degenerative diseases, e.g., for evaluating the effect of interventions to treat such diseases.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transgenic mouse having a recombinant nucleic acid molecule stably integrated into the genome of said mouse, said nucleic acid molecule comprising:
   (i) a strong ubiquitous promoter;
   (ii) downstream of said strong ubiquitous promoter, a conditional-STOP cassette comprising a coding region of a protein and polyadenylation signal, flanked on either side by a recombinase recognition site; and
   (iii) downstream of said conditional-STOP cassette, a sequence encoding a fusion protein comprising a caspase linked in frame with a FK Binding Protein (FKBP) or variant thereof, wherein said fusion protein is not expressed when said conditional-STOP cassette is present in the construct, wherein
   expression of a recombinase in an auditory hair cell of the mouse results in expression of the fusion protein in the auditory hair cell, and exposure of the mouse to an FKBP dimerizing agent results in hearing loss in the mouse; or
   expression of a recombinase in pancreatic beta cell of the mouse results in expression of the fusion protein, and exposure of the mouse to an FKBP dimerizing agent results in an increase in a blood glucose level in the mouse.

2. The transgenic mouse of claim 1, wherein said recombinant nucleic acid molecule is operably linked to one or more additional regulatory sequences.

3. A cell isolated from the transgenic mouse of claim 1 having a recombinant nucleic acid molecule stably integrated into the genome of said cell, said recombinant nucleic acid molecule comprising:
   (i) a strong ubiquitous promoter;
   (ii) downstream of said strong ubiquitous promoter, a conditional-STOP cassette comprising a coding region of a protein and polyadenylation signal, flanked on either side by a recombinase recognition site; and
   (iii) downstream of said conditional-STOP cassette, a sequence encoding a fusion protein comprising a caspase linked in frame with a FK Binding Protein (FKBP) or variant thereof, wherein said fusion protein is not expressed when said conditional-STOP cassette is present in the construct, wherein
   expression of a recombinase in said cell results in expression of the fusion protein in the cell.

4. The cell of claim 3, wherein said cell is a stem cell or a germ cell.

5. The transgenic mouse of claim 1, wherein the caspase is caspase 3.

6. A method for the production of a transgenic mouse of claim 1, comprising introduction of a recombinant nucleic acid molecule into a germ cell, an embryonic cell, or an egg cell, a recombinant nucleic acid molecule comprising:
  (i) a strong ubiquitous promoter;
  (ii) downstream of said strong ubiquitous promoter, a conditional-STOP cassette including a coding region of a protein and polyadenylation signal, flanked on either side by a recombinase recognition site; and
  (iii) downstream of said conditional-STOP cassette, a sequence encoding a fusion protein comprising a caspase linked in frame with a FK Binding Protein (FKBP) or variant thereof, wherein said fusion protein is not expressed when said conditional-STOP cassette is present in the construct.

7. The method of claim 6, further comprising crossing said transgenic mouse with a second mouse, wherein an auditory hair cell or a pancreatic beta cell of said second mouse express a recombinase that binds to and excises said stop sequence.

8. The transgenic mouse of claim 1, wherein said strong ubiquitous promoter is a CMV, β-actin, or ROSA26 promoter.

9. The transgenic mouse of claim 1, wherein expression of a recombinase in an auditory hair cell of the mouse results in expression of the fusion protein in the auditory hair cell, and exposure of the mouse to an FKBP dimerizing agent results in hearing loss in the mouse.

10. The transgenic mouse of claim 9, wherein the mouse expresses a recombinase in an auditory hair cell.

11. The transgenic mouse of claim 10, wherein the recombinase is expressed from a cell-specific promoter.

12. The transgenic mouse of claim 10, wherein the recombinase is cyclization recombination (Cre) recombinase or flippase (Flp) recombinase.

13. The transgenic mouse of claim 11, wherein the cell-specific promoter is Brn3c.

14. The transgenic mouse of claim 1, wherein expression of a recombinase in a pancreatic beta cell of the mouse results in expression of the fusion protein, and exposure of the mouse to an FKBP dimerizing agent results in an increase in a blood glucose level in the mouse.

15. The transgenic mouse of claim 14, wherein the mouse expresses a recombinase in a pancreatic beta cell.

16. The transgenic mouse of claim 15, wherein the recombinase is expressed from a cell-specific promoter.

17. The transgenic mouse of claim 15, wherein the recombinase is cyclization recombination (Cre) recombinase or flippase (Flp) recombinase.

18. The transgenic non-human mouse of claim 16, wherein the cell-specific promoter is the insulin promoter.

19. The method of claim 7, wherein the recombinase is cyclization recombination (Cre) recombinase or flippase (Flp) recombinase.

* * * * *

UNITED STATES PATENT AND TRADEMARK OFFICE
CERTIFICATE OF CORRECTION

PATENT NO. : 8,921,642 B2  
APPLICATION NO. : 12/352515  
DATED : December 30, 2014  
INVENTOR(S) : Albert Edge and Masato Fujioka Page 1 of 1

It is certified that error appears in the above-identified patent and that said Letters Patent is hereby corrected as shown below:

In the Claims

In column 58, line 23, in claim 18, delete "non-human mouse" and insert -- mouse --

Signed and Sealed this
Ninth Day of June, 2015

Michelle K. Lee
*Director of the United States Patent and Trademark Office*